United States Patent
Deisseroth et al.

(10) Patent No.: US 11,007,374 B2
(45) Date of Patent: May 18, 2021

(54) SYSTEM FOR OPTICAL STIMULATION OF TARGET CELLS

(71) Applicant: The Board of Trustees of the Leland Stanford Junior University, Stanford, CA (US)

(72) Inventors: Karl Deisseroth, Stanford, CA (US); Feng Zhang, Cambridge, MA (US); Edward Boyden, Cambridge, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 154 days.

(21) Appl. No.: 16/448,608

(22) Filed: Jun. 21, 2019

(65) Prior Publication Data

US 2019/0388705 A1    Dec. 26, 2019

Related U.S. Application Data

(63) Continuation of application No. 16/126,895, filed on Sep. 10, 2018, now Pat. No. 10,369,378, which is a
(Continued)

(51) Int. Cl.
*A61N 5/06*    (2006.01)
*C12N 13/00*    (2006.01)
(Continued)

(52) U.S. Cl.
CPC ............. *A61N 5/06* (2013.01); *A61N 5/0601* (2013.01); *A61N 5/0613* (2013.01);
(Continued)

(58) Field of Classification Search
CPC ...... A61N 5/06; A61N 5/0601; A61N 5/0613; A61N 5/0622; A61N 2005/0626;
(Continued)

(56) References Cited

U.S. PATENT DOCUMENTS 2,968,302 A    1/1961 Fry et al.
3,131,690 A    5/1964 Innis et al.
(Continued)

FOREIGN PATENT DOCUMENTS

CN    1079464 A    12/1993
CN    1558222 A    12/2004
(Continued)

OTHER PUBLICATIONS

Abbott et al., (2009) "Photostimulation of Retrotrapezoid Nucleus Phox2b-Expressing Neurons In Vivo Produces Long-Lasting Activation of Breathing in Rats", The Journal of Neuroscience 29(18):5806-5819.
(Continued)

*Primary Examiner* — Aaron F Roane
(74) *Attorney, Agent, or Firm* — Rudy J. Ng; Paula A. Borden; Bozicevic, Field & Francis LLP

(57) ABSTRACT

Various systems and methods are implemented for controlling stimulus of a cell. One such method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

13 Claims, 4 Drawing Sheets

Specification includes a Sequence Listing.

Related U.S. Application Data continuation of application No. 15/623,081, filed on Jun. 14, 2017, now Pat. No. 10,105,551, which is a continuation of application No. 15/229,064, filed on Aug. 4, 2016, now abandoned, which is a continuation of application No. 14/886,763, filed on Oct. 19, 2015, now abandoned, which is a continuation of application No. 14/665,978, filed on Mar. 23, 2015, now Pat. No. 9,187,745, which is a continuation of application No. 14/219,547, filed on Mar. 19, 2014, now abandoned, which is a continuation of application No. 13/763,119, filed on Feb. 8, 2013, now Pat. No. 8,864,805, which is a continuation of application No. 12/522,520, filed as application No. PCT/US2008/050745 on Jan. 10, 2008, now Pat. No. 8,398,692.

(60) Provisional application No. 60/903,248, filed on Feb. 23, 2007, provisional application No. 60/879,669, filed on Jan. 10, 2007.

(51) Int. Cl.
    *C12N 5/071*     (2010.01)
    *G01N 33/50*     (2006.01)
    *G01N 33/68*     (2006.01)

(52) U.S. Cl.
    CPC ......... *A61N 5/0622* (2013.01); *C12N 5/0602* (2013.01); *C12N 13/00* (2013.01); *G01N 33/502* (2013.01); *G01N 33/6872* (2013.01); *A61N 2005/0626* (2013.01); *A61N 2005/0647* (2013.01); *A61N 2005/0652* (2013.01); *A61N 2005/0663* (2013.01); *A61N 2005/0665* (2013.01)

(58) Field of Classification Search
    CPC .... A61N 2005/0647; A61N 2005/0652; A61N 2005/0663; A61N 2005/0665; C12N 5/0602; C12N 13/00; G01N 33/502; G01N 33/6872
    USPC .......................................................... 607/92
    See application file for complete search history.

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,696,722 B2 | 4/2014 | Deisseroth et al. |
| 8,716,447 B2 | 5/2014 | Deisseroth et al. |
| 8,815,582 B2 | 8/2014 | Deisseroth et al. |

(56) References Cited

U.S. PATENT DOCUMENTS

| | | | |
|---|---|---|---|
| 8,906,360 B2 * | 12/2014 | Deisseroth | A61P 5/50 424/93.2 |
| 8,926,959 B2 | 1/2015 | Deisseroth et al. | |
| 8,932,562 B2 | 1/2015 | Deisseroth et al. | |
| 9,057,734 B2 | 6/2015 | Cohen | |
| 9,079,940 B2 | 7/2015 | Deisseroth et al. | |
| 9,175,095 B2 | 11/2015 | Deisseroth et al. | |
| 9,249,234 B2 | 2/2016 | Deisseroth et al. | |
| 9,309,296 B2 | 4/2016 | Deisseroth et al. | |
| 9,340,589 B2 | 5/2016 | Deisseroth et al. | |
| 9,359,449 B2 | 6/2016 | Deisseroth et al. | |
| 9,421,258 B2 | 8/2016 | Deisseroth et al. | |
| 9,458,208 B2 | 10/2016 | Deisseroth et al. | |
| 9,522,288 B2 | 12/2016 | Deisseroth et al. | |
| 9,604,073 B2 | 3/2017 | Deisseroth et al. | |
| 9,636,380 B2 | 5/2017 | Deisseroth et al. | |
| 9,850,290 B2 | 12/2017 | Deisseroth et al. | |
| 9,968,652 B2 | 5/2018 | Deisseroth et al. | |
| 10,064,912 B2 | 9/2018 | Deisseroth et al. | |
| 10,071,132 B2 | 9/2018 | Deisseroth et al. | |
| 2001/0023346 A1 | 9/2001 | Loeb | |
| 2002/0094516 A1 | 7/2002 | Calos et al. | |
| 2002/0155173 A1 | 10/2002 | Chopp et al. | |
| 2002/0164577 A1 | 11/2002 | Tsien et al. | |
| 2002/0190922 A1 | 12/2002 | Tsao | |
| 2002/0193327 A1 | 12/2002 | Nemerow et al. | |
| 2003/0009103 A1 | 1/2003 | Yuste et al. | |
| 2003/0026784 A1 | 2/2003 | Koch et al. | |
| 2003/0040080 A1 | 2/2003 | Miesenbock et al. | |
| 2003/0050258 A1 | 3/2003 | Calos | |
| 2003/0082809 A1 | 5/2003 | Quail et al. | |
| 2003/0088060 A1 | 5/2003 | Benjamin et al. | |
| 2003/0097122 A1 | 5/2003 | Ganz et al. | |
| 2003/0103949 A1 | 6/2003 | Carpenter et al. | |
| 2003/0104512 A1 | 6/2003 | Freeman et al. | |
| 2003/0125719 A1 | 7/2003 | Furnish | |
| 2003/0144650 A1 | 7/2003 | Smith | |
| 2003/0204135 A1 | 10/2003 | Bystritsky | |
| 2003/0232339 A1 | 12/2003 | Shu et al. | |
| 2004/0013645 A1 | 1/2004 | Monahan et al. | |
| 2004/0015211 A1 | 1/2004 | Nurmikko et al. | |
| 2004/0023203 A1 | 2/2004 | Miesenbock et al. | |
| 2004/0034882 A1 | 2/2004 | Vale et al. | |
| 2004/0039312 A1 | 2/2004 | Hillstead et al. | |
| 2004/0049134 A1 | 3/2004 | Tosaya et al. | |
| 2004/0068202 A1 | 4/2004 | Hansson et al. | |
| 2004/0073278 A1 | 4/2004 | Pachys | |
| 2004/0076613 A1 | 4/2004 | Mazarkis et al. | |
| 2004/0122475 A1 | 6/2004 | Myrick et al. | |
| 2004/0203152 A1 | 10/2004 | Calos | |
| 2004/0216177 A1 | 10/2004 | Jordan et al. | |
| 2004/0260367 A1 | 12/2004 | Taboada et al. | |
| 2004/0267118 A1 | 12/2004 | Dawson | |
| 2005/0020945 A1 | 1/2005 | Tosaya et al. | |
| 2005/0027284 A1 | 2/2005 | Lozano et al. | |
| 2005/0058987 A1 | 3/2005 | Shi et al. | |
| 2005/0088177 A1 | 4/2005 | Schreck et al. | |
| 2005/0102708 A1 | 5/2005 | Lecanu et al. | |
| 2005/0107753 A1 | 5/2005 | Rezai et al. | |
| 2005/0112759 A1 | 5/2005 | Radisic et al. | |
| 2005/0119315 A1 | 6/2005 | Fedida et al. | |
| 2005/0124897 A1 | 6/2005 | Chopra | |
| 2005/0143295 A1 | 6/2005 | Walker et al. | |
| 2005/0143790 A1 | 6/2005 | Kipke et al. | |
| 2005/0153885 A1 | 7/2005 | Yun et al. | |
| 2005/0197679 A1 | 9/2005 | Dawson | |
| 2005/0202398 A1 | 9/2005 | Hegemann et al. | |
| 2005/0215764 A1 | 9/2005 | Tuszynski et al. | |
| 2005/0240127 A1 | 10/2005 | Seip et al. | |
| 2005/0267011 A1 | 12/2005 | Deisseroth et al. | |
| 2005/0267454 A1 | 12/2005 | Hissong et al. | |
| 2005/0279354 A1 | 12/2005 | Deutsch et al. | |
| 2006/0025756 A1 | 2/2006 | Francischelli et al. | |
| 2006/0034943 A1 | 2/2006 | Tuszynski | |
| 2006/0057192 A1 | 3/2006 | Kane | |
| 2006/0057614 A1 | 3/2006 | Heintz | |
| 2006/0058671 A1 | 3/2006 | Vitek et al. | |
| 2006/0058678 A1 | 3/2006 | Vitek et al. | |
| 2006/0100679 A1 | 5/2006 | DiMauro et al. | |
| 2006/0106543 A1 | 5/2006 | Deco et al. | |
| 2006/0129126 A1 | 6/2006 | Kaplitt et al. | |
| 2006/0155348 A1 | 7/2006 | de Charms | |
| 2006/0161227 A1 | 7/2006 | Walsh et al. | |
| 2006/0167500 A1 | 7/2006 | Towe et al. | |
| 2006/0179501 A1 | 8/2006 | Chan et al. | |
| 2006/0184069 A1 | 8/2006 | Vaitekunas | |
| 2006/0190044 A1 | 8/2006 | Libbus et al. | |
| 2006/0206172 A1 | 9/2006 | DiMauro et al. | |
| 2006/0216689 A1 | 9/2006 | Maher et al. | |
| 2006/0236525 A1 | 10/2006 | Sliwa et al. | |
| 2006/0241697 A1 | 10/2006 | Libbus et al. | |
| 2006/0253177 A1 | 11/2006 | Taboada et al. | |
| 2006/0271024 A1 | 11/2006 | Gertner et al. | |
| 2007/0027443 A1 | 2/2007 | Rose et al. | |
| 2007/0031924 A1 | 2/2007 | Li et al. | |
| 2007/0053996 A1 | 3/2007 | Boyden et al. | |
| 2007/0054319 A1 | 3/2007 | Boyden et al. | |
| 2007/0060915 A1 | 3/2007 | Kucklick | |
| 2007/0060984 A1 | 3/2007 | Webb et al. | |
| 2007/0135875 A1 | 6/2007 | Demarais et al. | |
| 2007/0156180 A1 | 7/2007 | Jaax et al. | |
| 2007/0191906 A1 | 8/2007 | Iyer et al. | |
| 2007/0196838 A1 | 8/2007 | Chesnut et al. | |
| 2007/0197918 A1 | 8/2007 | Vitek et al. | |
| 2007/0219600 A1 | 9/2007 | Gertner et al. | |
| 2007/0220628 A1 | 9/2007 | Glassman et al. | |
| 2007/0239080 A1 | 10/2007 | Schaden et al. | |
| 2007/0239210 A1 | 10/2007 | Libbus et al. | |
| 2007/0253995 A1 | 11/2007 | Hildebrand | |
| 2007/0260295 A1 | 11/2007 | Chen et al. | |
| 2007/0261127 A1 | 11/2007 | Boyden et al. | |
| 2007/0282404 A1 | 12/2007 | Cottrell et al. | |
| 2007/0295978 A1 | 12/2007 | Coushaine et al. | |
| 2008/0020465 A1 | 1/2008 | Padidam | |
| 2008/0027505 A1 | 1/2008 | Levin et al. | |
| 2008/0033569 A1 | 2/2008 | Ferren et al. | |
| 2008/0046053 A1 | 2/2008 | Wagner et al. | |
| 2008/0050770 A1 | 2/2008 | Zhang et al. | |
| 2008/0051673 A1 | 2/2008 | Kong et al. | |
| 2008/0060088 A1 | 3/2008 | Shin et al. | |
| 2008/0065158 A1 | 3/2008 | Ben-Ezra et al. | |
| 2008/0065183 A1 | 3/2008 | Whitehurst et al. | |
| 2008/0077200 A1 | 3/2008 | Bendett et al. | |
| 2008/0085265 A1 * | 4/2008 | Schneider | A61K 48/0083 424/93.21 |
| 2008/0088258 A1 | 4/2008 | Ng | |
| 2008/0103551 A1 | 5/2008 | Masoud et al. | |
| 2008/0119421 A1 | 5/2008 | Tuszynski et al. | |
| 2008/0125836 A1 | 5/2008 | Streeter et al. | |
| 2008/0167261 A1 | 7/2008 | Sclimenti | |
| 2008/0175819 A1 | 7/2008 | Kingsman et al. | |
| 2008/0176076 A1 | 7/2008 | Van Veggel et al. | |
| 2008/0200749 A1 | 8/2008 | Zheng et al. | |
| 2008/0221452 A1 | 9/2008 | Njemanze | |
| 2008/0227139 A1 | 9/2008 | Deisseroth et al. | |
| 2008/0228244 A1 | 9/2008 | Pakhomov et al. | |
| 2008/0262411 A1 | 10/2008 | Dobak | |
| 2008/0287821 A1 | 11/2008 | Jung et al. | |
| 2008/0290318 A1 | 11/2008 | Van Veggel et al. | |
| 2009/0030930 A1 | 1/2009 | Pradeep et al. | |
| 2009/0054954 A1 | 2/2009 | Foley et al. | |
| 2009/0069261 A1 | 3/2009 | Dodge et al. | |
| 2009/0088680 A1 | 4/2009 | Deisseroth et al. | |
| 2009/0093403 A1 | 4/2009 | Zhang et al. | |
| 2009/0099038 A1 | 4/2009 | Deisseroth et al. | |
| 2009/0131837 A1 | 5/2009 | Granville | |
| 2009/0148861 A1 | 6/2009 | Pegan et al. | |
| 2009/0157145 A1 | 6/2009 | Cauller | |
| 2009/0254134 A1 | 10/2009 | Nikolov et al. | |
| 2009/0268511 A1 | 10/2009 | Birge et al. | |
| 2009/0306474 A1 | 12/2009 | Wilson | |
| 2009/0319008 A1 | 12/2009 | Mayer | |
| 2009/0326603 A1 | 12/2009 | Boggs et al. | |
| 2010/0009444 A1 | 1/2010 | Herlitze et al. | |

(56) References Cited

U.S. PATENT DOCUMENTS

| | | |
|---|---|---|
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0165681 A1 | 7/2011 | Boyden et al. |
| 2011/0166632 A1 | 7/2011 | Delp et al. |
| 2011/0221970 A1 | 9/2011 | Kawabata et al. |
| 2011/0224095 A1 | 9/2011 | Zoller et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| CN | 1781019 A | 5/2006 |
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 9505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Adamantidis et al., (2011) "Optogenetic Interrogation of Dopaminergic Modulation of the Multiple Phases of Reward-Seeking Behavior", J. Neurosci. 31(30):10829-10835.

Aebischer et al., (1991) "Long-Term Cross-Species Brain Transplantation of a Polymer-Encapsulated Dopamine-Secreting Cell Line", Experimental Neurology 111:269-275.

Ageta-Ishihara et al., (2013) "Chronic Overload of SEPT4, a Parkin Substrate that Aggregates in Parkinson's Disease, Cause Behavioral Alterations but not Neurodegeneration in Mice", Molecular Brain vol. 6, 14 pages.

Ahmad et al., (2007) "The *Drosophila rhodopsin* Cytoplasmic Tail Domain is Required for Maintenance of Rhabdomere Structure", The FASEB Journal vol. 21, p. 449-455.

Ahmad et al., (2006) "Heterplogous Expression of Bovine Rhodopsin in *Drosophila* Photoreceptor Cells", Invest Ophthalmol Vis Sci. pp. 3722-3728.

Airan et al., (2009) "Temporally Precise In Vivo Control of Intracellular Signaling" Nature 458(7241):1025-1029.

Airan et al., (2007) "Integration of Light-Controlled Neuronal Firing and Fast Circuit Imaging", Current Opinion in Neurobiology 17:587-592.

Akirav et al., (2007) "The Role of the Medial Prefrontal Cortex-Amygdala Circuit in Stress Effects on the Extinction of Fear", Neural Plasticity: vol. 2007 Article ID:30873:1-11.

Ali "Gene and Stem Cell Therapy for Retinal Disorders"; vision-research.en—The Gateway to European Vision Research; accessed from http://www.visionresearch.eu/index.php?id=696, 10 pages (accessed Jul. 24, 2015).

Alilain et al., (2008) "Light-Induced Rescue of Breathing after Spinal Cord Injury", The Journal of Neuroscience 28(46):11862-11870.

Ang et al., (2005) "Hippocampal CA1 Circuitry Dynamically Gates Direct Cortical Inputs Preferentially at Theta Frequencies", The Journal of Neurosurgery 25(42):9567-9580.

Araki et al., (2002) "Site-Directed Integration of the cre Gene Mediated by Cre Recombinase Using a Combination of Mutant lox Sites", Nucleic Acids Research 30(19):1-8.

Aravanis et al., (2007) "An Optical Neural Interface: In Vivo Control of Rodent Motor Cortex with Integrated Fiberoptic and Optogenetic Technology", J. Neural. Eng. 4(3):S143-S156.

Arenkiel et al., (2007) "In Vivo Light-Induced Activation of Neural Circuitry in Transgenic Mice Expressing Channelrhodopsin-2", Neuron 54:205-218.

(56) References Cited

OTHER PUBLICATIONS

Argos et al., (1986) "The Integrase Family of Site-Specific Recombinases: Regional Similarities and Global Diversity", The EMBO Journal 5(2):433-440.
Asano et al., (2012) "Optically Controlled Contraction of Photosensitive Skeletal Muscle Cells", Biotechnology & Bioengineering 109(1):199-204.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Azizgolshani et al., (2013) "Reconstituted Plant Viral Capsids Can Release Genes to Mammalian Cells", Virology 441(1):12-17.
Babin et al., (2014) "Zebrafish Models of Human Motor Neuron Diseases: Advantages and Limitations", Progress in Neurobiology 118:36-58.
Balint et al., (2004) "The Nitrate Transporting Photochemical Reaction Cycle of the Pharanois Halorhodopsin", Biophysical Journal 86:1655-1663.
Bamberg et al., (1993) "Light-Driven Proton or Chloride Pumping by Halorhodopsin." Proc. Natl. Academy Science USA 90(2): 639-643.
Banghart et al., (2004) "Light-Activated Ion Channels for Remote Control of Neuronal Firing". Nature Neuroscience 7(12):1381-1386.
Barchet et al., (2009)"Challenges and Opportunities in CNS Delivery of Therapeutics for Neurodegenerative Diseases", Expert Opinion on Drug Delivery 6(3): 211-225.
Basil et al., (2005) "Is There Evidence for Effectiveness of Transcranial Magnetic Stimulation in the Treatment of Psychiatric Disorders?", Psychiatry 1(11): 64-69.
Bebbington et al., (1987) "The Use of Vectors Based on Gene Amplification for the Expression of Cloned Genes in Mammalian Cells in DNA Cloning" vol. 3, pp. 163-188.
Belzung et al., (2014) "Optogenetics to Study the Circuits of Fear- and Depression-like Behaviors: A Critical Analysis", Pharmacology, Biochemistry and Behavior 122:144-157.
Benabid (2000) "Future Strategies to Restore Brain Functions", Conference Proceedings from Medicine Meets Millennium: World Congress of Medicine and Health pp. 1-6.
Benoist et al., (1981) "In Vivo Sequence Requirements of the SV40 Early Promotor Region", Nature 290(5804):304-310.
Berges et al., (2007) "Transduction of Brain by Herpes Simplex Virus Vectors", Molecular Therapy (15)1: 20-29.
Berke et al., (2000) "Addiction, Dopamine, and the Molecular Mechanisms of Memory", Molecular Plasticity vol. 25: pp. 515-532.
Berlanga et al., (2003) "Cholinergic Interneurons of the Nucleus Accumbens and Dorsal Striatum are Activated by the Self-Administration of Cocaine", Neuroscience 120:1149-1156.
Berndt et al., (2008) "Bi-Stable Neural State Switches", Nature Neuroscience 12(2):229-234.
Berndt et al., (2014) "Structure-Guided Transformation of Channelrhodopsin into a Light-Activated Chloride Channel", Science 344:420-424.
Bernstein & Boyden (2011) "Optogenetic Tools for Analyzing the Neural Circuits of Behavior", Trends Cogn Sci. 15(12): 592-600.
Berridge et al., (2000) "The Versatility and Universality of Calcium Signaling", Nature Reviews: Molecular Cell Biology vol. 1: pp. 11-21.
Bi et al., (2006) "Ectopic Expression of a Microbial-Type Rhodopsin Restores Visual Responses in Mice with Photoreceptor Degeneration", Neuron 50(1):23-33.
Bi et al., (1998) "Synaptic Modifications in Cultured Hippocampal Neurons: Dependence on Spike Timing, Synaptic Strength, and Postsynaptic Cell Type", Journal of Neuroscience 18(24):10464-10472.
Bibel et al., (2004) "Differentiation of Mouse Embryonic Stem Cells into a Defined Neuronal Lineage", Nature Neuroscience 7(9):1033-1009.
Blomer et al., (1997) "Highly Efficient and Sustained Gene Transfer in Adult Neurons with Lentivirus Vector", Journal of Virology 71(9):6641-6649.
Bocquet et al., (2007) "A Prokaryotic Proton-Gated Ion Channel from the Nicotinic Acetylcholine Receptor Family", Nature Letters 445:116-119.
Bowers et al., (2011) "Genetic Therapy for the Nervous System", Human Molecular Genetics 20(1): R28-R41.
Boyden et al., (2005) "Millisecond-Timescale, Genetically Targeted Optical Control of Neural Activity" Nature Neuroscience 8(9):1263-1268.
Boyden et al., (2011) "A History of Optogenetics: The Development of Tools for Controlling Brain Circuits with Light", F1000 Biology Reports 3(11):12 pages.
Braun (1999) "Two Light-Activated Conductances in the Eye of the Green Alga Volvox Carteri", Biophys J. 76(3):1668-1678.
Brewin (2011) "The Nature and Significance of Memory Disturbance in Posttraumatic Stress Disorder"; Ann. Rev. Clin. Psychol. vol. 7:203-227.
Brinton et al., (2006) "Preclinical Analyses of the Therapeutic Potential of Allopregnanolone to Promote Neurogenesis In Vitro and In Vivo in Transgenic Mouse Model of Alzheimer's Disease", Current Alzheimer Research 3(1):11-17.
Brosenitsch et al., (2001) "Physiological Patterns of Electrical Stimulation Can Induce Neuronal Gene Expression by Activating N-Type Calcium Channels", Journal of Neuroscience 21(8):2571-2579.
Brown et al., (2000) "Long-Term Potentiation Induced by θ Frequency Stimulation is Regulated by a Protein Phosphate-Operated Gate", The Journal of Neuroscience 20(21):7880-7887.
Bruegmann et al., (2010) "Optogenetic Control of Heart Muscle In Vitro and In Vivo", Nature Methods 7(11): 897-900.
Bruegmann et al., (2011) "Optogenetics in Cardiovascular Research: A New Tool for Light-Induced Depolarization of Cardiomyocytes and Vascular Smooth Muscle Cells In Vitro and In Vivo", European Heart Journal vol. 32 No. Suppl 1, p. 997.
Callaway et al., (1993) "Photostimulation Using Caged Glutamate Reveals Functional Circuitry in Living Brain Slices", Proc. Natl. Acad. Sci. USA vol. 90:7661-7665.
Campagnola et al., (2008) "Fiber-Coupled Light-Emitting Diode for Localized Photostimulation of Neurons Expressing Channelrhodopsin-2", Journal of Neuroscience Methods 169(1) Abstract only.
Cannon et al., (2006) "Endophenotypes in the Genetic Analyses of Mental Disorders", Annu. Rev. Clin. Psychol. vol. 2:267-290.
Cardin et al., (2009) "Driving Fast spiking Cells Induces Gamma Rhythm and Controls Sensory Responses" Nature 459(7247):663-667.
Cardin et al., (2010) "Targeted Optogenetic Stimulation and Recording of Neurons In Vivo Using Cell-Type-Specific Expression of Channelrhodopsin-2", Nature Protocols 5(2):247-254.
Caro et al., (2012) "Engineering of an Artificial Light-Modulated Potassium Channel", PLoS One 7(8):e43766.
Castagne et al., (2010) "Rodent Models of Depression: Forced Swim and Tail Suspension Behavioral Despair Tests in Rats and Mice", Current Protocols in Pharmacology Supp. 49 Unit 5.8.1-5.8.14.
Cazillis et al., (2004) "VIP and PACAP Induce Selective Neuronal Differentiation of Mouse Embryonic Stem Cells", Eur J Neurosci. 19(4):798-808.
Cenatiempo (1986) "Prokaryotic Gene Expression In Vitro: Transcription-Translation Coupled Systems", Biochimie. 68(4):505-515.
Chamanzar et al., (2015) "Deep Tissue Targeted Near-infrared Optogenetic Stimulation using Fully Implantable Upconverting Light Bulbs", 2015 37th Annual International Conference of the IEEE Engineering in Medicine and Biology Society (EMBC), IEEE; pp. 821-824.
Chinta et al., (2005) "Dopaminergic Neurons", The International Journal of Biochemistry & Cell Biology 37: 942-946.
Chow et al., (2013) "Optogenetics and Translation Medicine", Sci Transl Med. 5(177):177.

(56) References Cited

OTHER PUBLICATIONS

Chow et al., (2010) "High-Performance Genetically Targetable Optical Neural Silencing by Light-Driven Proton Pumps", Nature 463: 98-102.

Clare 2008 "Functional Expression of Ion Channels in Mammalian Systems", Protein Science Encyclopedia A.R. Fersht (Ed.) pp. 79-109.

Clare (2010) "Targeting Ion Channels for Drug Discovery", Discov Med. 9(46):1-6.

Clark et al., (2003) "A Future for Transgenic Livestock", Nature Reviews Genetics 4(10):825-833.

Claudio et al., (1983) "Nucleotide and Deduced Amino Acid Sequences of Torpedo Californica Acetylcholine Receptor Gamma Subunit", PNAS USA 80:1111-1115.

Coleman et al., (2014) "Assessing Anxiety in Nonhuman Primates", Ilar Journal 55(2):333-346.

Collingridge et al., (1984) "Inhibitory Post-Synaptic Currents in Rat Hippocampal CA1 Neurones", J. Physiol. 356:551-564.

Covington et al., (2010) "Antidepressant Effect of Optogenetic Stimulation of the Medial Prefrontal Cortex", Journal of Neuroscience 30(48):16082-16090.

Cowan et al., (2003) "Targeting Gene Expression to Endothelium in Transgenic Animals: A Comparison of the Human ICAM-2, PECAM-1, and Endoglin Promoters", Xenotransplantation 10:223-231.

Crouse et al., (1983) "Expression and Amplification of Engineered Mouse Dihydrofolate Reductase Minigenes", Mol. Cell. Biol. 3(2):257-266.

Cucchiaro et al., (1991) "Electron-Microscopic Analysis of Synaptic Input from the Perigeniculate Nucleus to A-Laminae of the Lateral Geniculate Nucleus in Cats", The Journal of Comparitive Neurology 310:316-336.

Cucchiaro et al., (1990) "Phaseolus Vulgaris Leucoagglutinin (PHA-L): A Neuroanatomical Tracer for Electron Microscopic Analysis of Synaptic Circuitry in the Cat's Dorsal Lateral Geniculate Nucleus", J. Electron. Microsc. Tech.15(4):352-368.

Cui et al., (2001) "Electrochemical Deposition and Characterization of Conducting Polymer Polypyrrole/PSS on Multichannel Neural Probes", Sensors and Actuators 93(1):8-18.

Dalva et al., (1994) "Rearrangements of Synaptic Connections in Visual Cortex Revealed by Laser Photostimulation", Science 265:255-258.

Daniel et al., (2016) "Stress Modulation of Opposing Circuits in the Bed Nucleus of the Stria Terminalis", Neuropsychopharmacology Reviews 41:103-125.

Date et al., (2000) "Grafting of Encapsulated Dopamine-Secreting Cells in Parkinson's Disease: Long-Term Primate Study", Cell Transplant 9:705-709.

Davidson et al., (2003) "Viral Vectors for Gene Delivery to the Nervous System", Nature Reviews Neuroscience 4:353-364.

Davis (1990) "The Many Faces of Epidermal Growth Factor Repeats", The New Biologist 2(5):410-419.

Day et al., (2007) "The Nucleus Accumbens and Pavlovian Reward Learning", Neuroscientist 13(2):148-159.

De Foubert et al., (2004) "Fluoxetine-Induced Change in Rat Brain Expression of Brain-Derived Neurotrophic Factor Varies Depending on Length of Treatment," Neuroscience 128:597-604.

De Palma et al., (2003) "In Vivo Targeting of Tumor Endothelial Cells by Systemic Delivery of Lentiviral Vectors", Human Gene Therapy 14:1193-1206.

Dederen et al., (1994) "Retrograde Neuronal Tracing with Cholera Toxin B Subunit: Comparison of Three Different Visualization Methods", Histochemical Journal 26:856-862.

Definition of Implant; Merriam-Webster Dictionary; retrieved Nov. 7, 2016 (http://www.merriam-webster.com/dictionary/implant).

Definition of Integral. Merriam-Webster Dictionary, retrieved on Mar. 20, 2017; Retrieved from the internet: (http://www.merriam-webster.com/dictionary/integral).

Definition of Psychosis (2015) Wikipedia, retrieved on Feb. 5, 2015 (http://en.wikipedia.org/wiki/psychosis).

Deisseroth (2006) "Next-Generation Optical Technologies for Illuminating Genetically Targeted Brain Circuits", The Journal of Neuroscience 26(41):10380-10386.

Deisseroth et al., (2004) "Excitation-neurogenesis Coupling in Adult Neural Stem/Progenitor Cells", Neuron 42:535-552.

Deisseroth et al., (1996) "Signaling from Synapse to Nucleus: Postsynaptic CREB Phosphorylation During Multiple Forms of Hippocampal Synaptic Plasticity", Neuron 16:89-101.

Deisseroth et al., (2003) "Signaling from Synapse to Nucleus: The Logic Behind the Mechanisms", Currrent Opinion in Neurobiology 13:354-365.

Deisseroth et al., (1998) "Translocation of Calmodulin to the Nucleus Supports CREB Phosphorylation in Hippocampal Neurons", Nature 392:198-202.

Deisseroth et al., (2010) "Controlling the Brain with Light", Scientific American 303:48-55.

Delaney et al., (1997) "Evidence for a Long-Lived 13-cis-Containing Intermediate in the Photocycle of the leu 93 → ala Bacteriorhodopsin Mutant", J. Physical Chemistry B 101(29):5619-5621.

Denk et al., (1994) "Anatomical and Functional Imaging of Neurons Using 2-Photon Laser Scanning Microscopy", Journal of Neuroscience Methods 54:151-162.

Deonarain (1998) "Ligand-Targeted Receptor-Mediated Vectors for Gene Delivery", Exp. Opin. Ther. Patents 8(1):53-69.

Ditterich et al., (2003) "Microstimulation of Visual Cortex Affects the Speed of Perceptual Decisions", Nature Neuroscience 6(8):891-898.

Dittgen et al., (2004) "Lentivirus-Based Genetic Manipulations of Cortical Neurons and their Optical and Electrophysiological Monitoring In Vivo", PNAS 101(52):18206-18211.

Do Carmo et al., (2013) "Modeling Alzheimer's Disease in Transgenic Rats", Molecular Neurodegeneration 8(37):11 pages.

Douglass et al., (2008) "Escape Behavior Elicited by Single, Channelrhodopsin-2-Evoked Spikes in Zebrafish Somatosensory Neurons", Curr Biol. 18(15):1133-1137.

Duvarci et al., (2009) "The Bed Nucleus of the Stria Terminalis Mediates Inter-Individual Variations in Anxiety and Fear", J. Neurosci. 29(33):10357-10361.

Ebert et al., (1988) "A Moloney MLV-rat Somatotropin Fusion Gene Produces Biologically Active Somatotropin in a Transgenic Pig", Mol. Endocrinology 2:277-283.

EBI accession No. EMBL: J05199; "N. pharaonis halorhodopsin (hop) gene, complete cds"; (Nov. 22, 1990).

EBI accession No. UNIPROT: A7U0Y6; "SubName: Full= Bacteriorhodopsin"; (Aug. 10, 2010).

EBI accession No. UNIPROT: B0R5N9; "Subname: Full= Bacteriorhodopsin"; (Apr. 8, 2008).

EBI accession No. UNIPROT: B4Y103; "SubName: Full= Channelrhodopsin-1"; (Sep. 23, 2008).

EBI accession No. UNIPROT: P15647; "RecName: Full= Halorhodopsin; Short=HR; Alt Name: Full=NpHR"; (Apr. 1, 1990).

Edelstein et al., (2004) "Gene Therapy Clinical Trials Worldwide 1989-2004—An Overview", The Journal of Gene Medicine 6:597-602.

Ehrlich et al., (2009) "Amygdala Inhibitory Circuits and the Control of Fear Memory", Neuron 62:757-771.

Eijkelkamp et al., (2012) "Neurological Perspectives on Voltage-Gated Sodium Channels", Brain 135:2585-2612.

Eisen (1999) "Treatment of Amyotrophic Lateral Sclerosis", Drugs Aging 14(3):173-196.

Emerich et al., (1992) "A Novel Approach to Neural Transplantation in Parkinson's Disease: Use of Polymer-Encapsulated Cell Therapy", Neuroscience and Biobehavioral Reviews 16:437-447.

Ensell et al., (2000) "Silicon-Based Microelectrodes for Neurophysiology, Micromachined from Silicon-on-Insulator Wafers", Med. Biol. Eng. Comput 38:175-179.

Erbguth et al., (2012) "Bimodal Activation of Different Neuron Classes with Spectrally Red-Shifted Channelrhodopsin Chimera C1V1 in Caenorhabditis Elegans", Plos One 7(10):e46827/1-9.

Ernst et al., (2008) "Photoactivation of Channelrhodopsin", J. Biol. Chem. 283(3):1637-1643.

(56) References Cited

OTHER PUBLICATIONS

Esposito et al., (1997) "The Integrase Family of Tyrosine Recombinases: Evolution of a Conserved Active Site Domain", Nucleic Acids Research 25(18):3605-3614.
Evanko (2007) "Optical Excitation Yin and Yang", Nature Methods 4:384.
Fabian et al., (1985) "Transneuronal Transport of Lectins", Brain Research 344:41-48.
Falconer et al., (2002) "High-Throughput Screening for Ion Channel Modulators", Journal of Biomolecular Screening 7(5):460-465.
Fanselow et al., (1999) "Why We Think Plasticity Underlying Pavlovian Fear Conditioning Occurs in the Basolateral Amygdala", Neuron 23:229-232.
Farber et al., (1983) "Identification of Presynaptic Neurons by Laser Photostimulation", Science 222:1025-1027.
Feng et al., (2000) "Imaging Neuronal Subsets in Transgenic Mice Expressing Multiple Spectral Variants of GFP", Neuron 28:41-51.
Fenno et al., (2011) "The Development and Application of Optogenetics", Annual Review of Neuroscience 34(1):389-412.
Ferenczi et al., (2016) "Optogenetic Approaches Addressing Extracellular Modulation of Neural Excitability", Scientific Reports 6:20 pages.
Fiala et al., (2010) "Optogenetic Approaches in Neuroscience", Current Biology 20(20):R897-R903.
Fisher et al., (2006) "Spatiotemporal Activity Patterns During Respiratory Rhythmogenesis in the Rat Ventrolateral Medulla", The Journal of Neurophysiol 95:1982-1991.
Fitzsimons et al., (2002) "Promotors and Regulatory Elements that Improve Adeno-Associated Virus Transgene Expression in the Brain", Methods 28:227-236.
Foster (2005) "Bright Blue Times", Nature 433:698-699.
Fox et al., (2005) "A Gene Neuron Expression Fingerprint of C. Elegans Embryonic Motor Neurons", BMC Genomics 6(42):1-23.
Friedman et al., (2009) "Programmed Acute Electrical Stimulation of Ventral Tegmental Area Alleviates Depressive-Like Behavior", Neuropsychopharmacology 34:1057-1066.
Friedman et al., (2008) "VTA Dopamine Neuron Bursting is Altered in an Animal Model of Depression and Corrected by Desipramine", J. Mol. Neurosci. 34:201-209.
Garrido et al., (2003) "A Targeting Motif Involved in Sodium Channel Clustering at the Axonal Initial Segment", Science 300(5628):2091-2094.
Gelvich et al., (2002) "Contact Flexible Microstrip Applicators (CFMA) in a Range from Microwaves up to Short Waves", IEEE Transactions on Biomedical Engineering 49(9):1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine D2 receptor 1-4, 24-25 gene, promoter region and exon 1. Jan. 31, 1997.
Gerits et al., (2012) "Optogenetically Induced Behavioral and Functional Network Changes in Primates", Current Biology 22:1722-1726.
Gigg et al., (1994) "Glutamatergic Hippocampal Formation Projections to Prefrontal Cortex in the Rat are Regulated by GABAergic Inhibition and Show Convergence with Glutamatergic Projections from the Limbic Thalamus", Hippocampus 4(2):189-198.
Gilman et al., (1984) "Isolation of Sigma-28-Specific Promoters from *Bacillus subtilis* DNA" Gene 32(1-2):11-20.
Glick et al., (1987) "Factors Affecting the Expression of Foreign Proteins in *Escherichia coli*", Journal of Industrial Microbiology 1(5):277-282.
Goekoop et al., (2006) "Cholinergic Challenge in Alzheimer Patients and Mild Cognitive Impairment Differentially Affects Hippocampal Activation—a Pharmacological fMRI Study", Brain 129:141-157.
Gold et al., (2000) "Representation of a Perceptual Decision in Developing Oculomotor Commands", Nature 404:390-394.
Gong et al., (2013) "Enhanced Archaerhodopsin Fluorescent Protein Voltage Indicators", PLOS One 8(6):10 pages.
Gonzalez et al., (1999) "Cell-Based Assays and Instrumentation for Screening Ion-Channel Targets", DDT 4(9): pp. 431439.
Gordon et al., (1987) "Regulation of Thy-1 Gene Expression in Transgenic Mice", Cell 50:445-452.
Gorelova et al., (1997) "The Course of Neural Projection from the Prefrontal Cortex to the Nucleus Accumbens in the Rat ", Neuroscience 76(3):689-706.
Goshen et al., (2011) "Dynamics of Retrieval Strategies for Remote Memories", Cell 147:678-589.
Gottesman et al., (1984) "Bacterial Regulation: Global Regulatory Networks", Ann. Rev. Genet 18:415-441.
Gradinaru et al., (2009) "Optical Deconstruction of Parkinsonian Neural Circuitry", Science 324(5925):354-359.
Gradinaru et al., (2007) "Targeting and Readout Strategies for Fast Optical Neural Control In Vitro and In Vivo", J Neuroscience 27(52):14231-14238.
Gradinaru et al., (2008) "eNpHR: A Natronomonas Halorhodopsin Enhanced for Optogenetic Applications", Brain Cell Biol. 36(1-4):129-139.
Gradinaru et al., (2010) "Molecular and Cellular Approaches for Diversifying and Extending Optogenetics", Cell 141(1):154-165.
Grady et al., (1995) "Age-Related Reductions in Human Recognition Memory Due to Impaired Encoding", Science 269(5221):218-221.
Greenberg et al., (2006) "Three-Year Outcomes in Deep Brain Stimulation for Highly Resistant Obsessive-Compulsive Disorder", Neuropsychopharmacology 31:2384-2393.
Gregory et al., (2003)"Integration Site for *Streptomyces* Phage φBT1 and Development of Site-Specific Integrating Vectors", Journal of Bacteriology 185(17):5320-5323.
Gritton et al., (2010) "Optogenetically-Evoked Cortical Cholinergic Transients in Mice Expressing Channelrhodopsin-2 (ChR2) in Cholinergic Neurons", Society for Neuroscience Abstract Viewer and Itinery Planner & 40th Annual Meeting of the Society-for-Neuroscience 40:2 pages.
Groth et al., (2004) "Phage Integrases: Biology and Applications", Journal of Molecular Biology 335:667-678.
Groth et al., (2000) "A Phage Integrase Directs Efficient Site-Specific Integration in Human Cells", PNAS 97(11):5995-6000.
Guatteo et al., (2005) "Temperature Sensitivity of Dopaminergic Neurons of the Substantia Nigra Pars Compacta: Involvement of Transient Receptor Potential Channels", Journal of Neurophysiol. 94:3069-3080.
Gulick et al., (1997) "Transfection using DEAE-Dextran" Supplement 40, Current Protocols in Molecular Biology Supplement 40, 9.2.1-9.2.10.
Gunaydin et al., (2010) "Ultrafast Optogenetic Control", Nature Neuroscience 13(3):387-392.
Gur et al., (1997) "A Dissociation Between Brain Activity and Perception: Chromatically Opponent Cortical Neurons Signal Chromatic Flicker that is not Perceived", Vision Research 37(4):377-382.
Hackmann et al., (2001) "Static and Time-Resolved Step-Scan Fourier Transform Infrared Investigations of the Photoreaction of Halorhodopsin from Natronobacterium Pharaonis: Consequences for Models of the Anion Translocation Mechanism", Biophysical Journal 81:394-406.
Hagglund et al., (2010)"Activation of Groups of Excitatory Neurons in the Mammalian Spinal Cord or Hindbrain Evokes Locomotion", Nature Neuroscience 13(2):8 pages.
Haim et al., (2006) "Gene Therapy to the Nervous System", Stem Cell and Gene-Based Therapy Section 2:133-154.
Hallet et al., (1997) "Transposition and Site-Specific Recombination: Adapting DNA Cut-and-Paste Mechanisms to a Variety of Genetic Rearrangements", FEMS Microbiology Reviews 21(2):157-178.

(56) References Cited

OTHER PUBLICATIONS

Hamer et al., (1982) "Regulation In Vivo of a Cloned Mammalian Gene: Cadmium Induces the Transcription of a Mouse Metallothionein Gene in SV40 Vectors", Journal of Molecular Applied Genetics 1(4):273-288.

Hammack et al., (2009) "The Response of Neurons in the Bed Nucleus of the Stria Terminalis to Serotonin Implications for Anxiety", Progress in Neuro-Psychopharmacology & Biological Psychiatry 33:1309-1320.

Hammer et al., (1990) "Spontaneous Inflammatory Disease in Transgenic Rats Expressing HLA-B27 and Human $\beta_2$m: An Animal Model of HLA-B27-Associated Human Disorders", Cell (63):1099-1112.

Han et al., (2011) "A High-Light Sensitivity Optical Neural Silencer: Development and Application to Optogenetic Control of Non-Human Primate Cortex", Frontiers in Systems Neuroscience 5(18):1-8.

Han et al., (2009) "Millisecond-Timescale Optical Control of Neural Dynamics in the Nonhuman Primate Brain", Neuron 62:191-198.

Han et al., (2007) "Multiple-Color Optical Activation, Silencing, and Desynchronization of Neural Activity with Single-Spike Temporal Resolution", PLoS One 2(3):1-12.

Han et al., (2012) "Optogenetics in the Nonhuman Primate", Prog. Brain Res. 196:215-233.

Han et al., (2007) "Two-Color, Bi-Directional Optical Voltage Control of Genetically-Targeted Neurons", CoSyne Abstract Presentation, Presented Feb. 24, 2007.

Han et al., (2012) "Virogenetic and Optogenetic Mechanisms to Define Potential Therapeutic Targets in Psychiatric Disorders", Neuropharmacology 62:89-100.

Hausser et al., (1997) "Tonic Synaptic Inhibition Modulates Neuronal Output Pattern and Spatiotemporal Synaptic Integration", Neuron 19:665-678.

Hegemann et al., (1991) "All-trans Retinal Constitutes the Functional Chromophore in *Chlamydomonas rhodopsin*", Biophys. J. 60:1477-1489.

Herlitze et al., (2007) "New Optical Tools for Controlling Neuronal Activity", Curr Opin Neurobiol. 17(1):87-94.

Herry et al., (2008) "Switching on and off Fear by Distinct Neuronal Circuits", Nature 454:600-606.

Heymann et al., (1997) "Expression of Bacteriorhodopsin in Sf9 and COS-1 Cells", Journal of Bioenergetics and Biomembranes 29(1):55-59.

Hikida et al., (2003) "Acetylcholine Enhancement in the Nucleus Accumbens Prevents Addictive Behaviors of Cocaine and Morphine", PNAS 100(10):6169-6173.

Hikida et al., (2001) "Increased Sensitivity to Cocaine by Cholingergic Cell Ablation in Nucleus Accumbens", PNAS 98(23):13351-13354.

Hildebrandt et al., (1993) "Bacteriorhodopsin Expressed in *Schizosaccharomyces pombe* Pumps Protons through the Plasma Membrane", PNAS 90:3578-3582.

Hira et al., (2009) "Transcranial Optogenetic Stimulation for Functional Mapping of the Motor Cortex", J Neurosci Methods 179:258-263.

Hirase et al., (2002) "Multiphoton Stimulation of Neurons", J Neurobiol. 51(3):237-247.

Hodaie et al., (2002) "Chronic Anterior Thalamus Stimulation for Intractable Epilepsy", Epilepsia 43:603-608.

Hoffman et al., (1997) "K+ Channel Regulation of Signal Propagation in Dendrites of Hippocampal Pyramidal Neurons", Nature 387:869-874.

Hofherr et al., (2005) "Selective Golgi export of Kir2.1 Controls the Stoichiometry of Functional Kir2.x Channel Heteromers", Journal of Cell Science 118:1935-1943.

Hosokawa et al., (2003) "Imaging Spatio-Temporal Patterns of Long-Term Potentiation in Mouse Hippocampus", Philos. Trans. R. Soc. Lond. B. 358:689-693.

Hososhima et al., (2015) "Near-Infrared (NIR) Up-Conversion Optogenetics", Optical Techniques in Neurosurgery, Neurophotonics, and Optogenetics II; vol. 9305:4 pages.

Hustler et al., (1996) "Acetylcholinesterase Staining in Human Auditory and Language Cortices: Regional Variation of Structural Features", Cereb Cortex 6(2):260-270.

Hynynen et al., (2007) "Clinical Applications of Focused Ultrasound—The Brain", Int. J. Hyperthermia 23(2):193-202.

Ibbini et al., (1989) "A Field Conjugation Method for Direct Synthesis of Hyperthermia Phased-Array Heating Patterns", IEEE Transactions on Ultrasonics, Ferroelectrics, and Frequency Control 36(1):3-9.

Ihara et al., (1999) "Evolution of the Archaeal Rhodopsins: Evolution Rate Changes by Gene Duplication and Functional Differentiation", J. Mol. Biol. 285:163-174.

International Search Report for International Application No. PCT/US2009/053474, dated Oct. 8, 2009.

Isenberg et al., (1989) "Cloning of a Putative Neuronal Nicotinic Aceylcholine Receptor Subunit", Journal of Neurochemistry 52(3):988-991.

Iyer et al., (2014) "Virally Mediated Optogenetic Excitation and Inhibition of Pain in Freely Moving Nontransgenic Mice", Nat Biotechnol. 32(3):274-278.

Jekely (2009) "Evolution of Phototaxis", Phil. Trans. R. Soc. B. 364:2795-2808.

Jennings et al., (2013) "Distinct Extended Amygdala Circuits for Divergent Motivational States", Nature 496:224-228.

Ji et al., (2012) "Light-Evoked Somatosensory Perception of Transgenic Rats that Express Channelrhodopsin-2 in Dorsal Root Ganglion Cells", PLoS One 7(3):e32699.

Jimenez & Maren et al (2009) "Nuclear Disconnection within the Amygdala Reveals a Direct Pathway to Fear", Learning Memory 16:766-768.

Johansen et al., (2010) "Optical Activation of Lateral Amygdala Pyramidal Cells Instructs Associative Fear Learning", PNAS 107(28):12692-12697.

Johnson et al., (2006) "Differential Biodistribution of Adenoviral Vector In Vivo as Monitored by Bioluminescence Imaging and Quantitative Polymerase Chain Reaction", Human Gene Therapy 17:1262-1269.

Johnson-Saliba et al., (2001) "Gene Therapy: Optimising DNA Delivery to the Nucleus", Current Drug Targets 2:371-399.

Johnston et al., (1982) "Isolation of the Yeast Regulatory Gene GAL4 and Analysis of its Dosage Effects on the Galactose/Melibiose Regulon," PNAS 79:6971-6975.

Jones et al., (2011) "Animal Models of Schizophrenia", British Journal of Pharmacology 164:1162-1194.

Kaiser (2007) "Clinical Research. Death Prompts a Review of Gene Therapy Vector", Science 317(5838):580, 1 page.

Kandel et al., (1961) "Electrophysiology of Hippocampal Neurons: I. Sequential Invasion and Synaptic Organization", J Neurophysiol. 24:225-242.

Kandel et al., (1961) "Electrophysiology of Hippocampal Neurons: II. After-Potentials and Repetitive Firing", J Neurophysiol. 24:243-259.

Karra, et al. (2010) "Transfection Techniques for Neuronal Cells", The Journal of Neuroscience 30(18):6171-6177.

Karreman et al., (1996) "On the use of Double FLP Recognition Targets (FRTs) in the LTR of Retroviruses for the Construction of High Producer Cell Lines", Nucleic Acids Research 24(9):1616-1624.

Kato et al., (1993) "Present and Future Status of Noninvasive Selective Deep Heating using RF in Hyperthermia", Med & Biol. Eng. & Comput 31 Supp: S2-11. Abstract. p. S2 only.

Katz et al.,(1994) "Scanning Laser Photostimulation: A New Approach for Analyzing Brain Circuits", Journal of Neuroscience Methods 54:205-218.

Kay (2011)"State-of-the-Art Gene-Based Therapies: The Road Ahead", Nature Reviews Genetics 12:316-328.

Kelder et al., (2001) "Glycoconjugates in Human and Transgenic Animal Milk", Advances in Exp. Med. and Biol. 501:269-278.

(56) References Cited

OTHER PUBLICATIONS

Kessler et al., (1996) "Gene Delivery to Skeletal Muscle Results in Sustained Expression and Systemic Delivery of a Therapeutic Protein", Proc. Natl. Acad. Sci. USA 93:14082-14087.
Khodakaramian et al., (2006) "Expression of Cre Recombinase during Transient Phage Infection Permits Efficient Marker Removal in *Streptomyces*", Nucleic Acids Research 34(3):e20:1-5.
Khosravani et al., (2006) "Voltage-Gated Calcium Channels and Idiopathic Generalized Epilepsies", Physiol. Rev. 86:941-966.
Kianianmomeni et al., (2009) "Channelrhodopsins of Volvox carteri are Photochromic Proteins that are Specifically Expressed in Somatic Cells under Control of Light, Temperature, and the Sex Inducer", Plant Physiology 151(1):347-366.
Kim et al., (2013) "Diverging Neural Pathways Assemble a Behavioural State from Separable Features in Anxiety", Nature 496(7444):219-23.
Kim et al., (2005) "Light-Driven Activation of β2-Adrenergic Receptor Signaling by a Chimeric Rhodopsin Containing the β2-Adrenergic Receptor Cytoplasmic Loops", Biochemistry 44(7):2284-2292.
Kim et al., (2004) "PDZ Domain Proteins of Synapses", Nature Reviews Neuroscience 5(10):771-781.
Kingston et al., (1999) "Transfection and Expression of Cloned DNA", Supplement 31, Current Protocols in Immunology 10.13.-1 0.13.9.
Kingston et al., (1996) "Transfection of DNA into Eukaryotic Cells", Supplement 63, Current Protocols in Molecular Biology 9.1.1-9.1.11, 11 pages.
Kinoshita et al., (2010) "Optogenetically Induced Supression of Neural Activity in the Macaque Motor Cortex", Poster Sessions Somatomotor System, Others, Society for Neuroscience Meeting pp. 141-154.
Kita et al., (1999) "Effects of Dopamine Agonists and Antagonists on Optical Responses Evoked in Rat Frontal Cortex Slices after Stimulation of the Subcortical White Matter", Exp. Brain Research 125:383-388.
Kitabatake et al., (2003) "Impairment of Reward-Related Learning by Cholinergic Cell Ablationn in the Striatum", PNAS 100(13):7965-7970.
Kitayama et al., (2004) "Regulation of Neuronal Differentiation by N-Methyl-D-Aspartate Receptors Expressed in Neural Progenitor Cells Isolated from Adult Mouse Hippocampus", Journal of Neurosci Research 76(5):599-612.
Klausberger et al., (2003) "Brain-State- and Cell-Type-Specific Firing of Hippocampal Interneurons In Vivo", Nature 421:844-848.
Kleinlogel et al., (2011) "A Gene-Fusion Strategy for Stoichiometric and Co-Localized Expression of Light-Gated Membrane Proteins", Nature Methods 8(12):1083-1091.
Knopfel et al., (2012) "A Comprehensive Concept of Optogenetics", Progress in Brain Research 196:1-28.
Knopfel et al., (2006) "Optical Probing of Neuronal Circuit Dynamics: Genetically Encoded Versus Classical Fluorescent Sensors", Trends Neurosci. 29(3):160-166.
Knopfel et al., (2010) "Remote Control of Cells", Nature Nanotechnology 5:560-561.
Knox et al., (2003) "Heterologous Expression of *Limulus* Rhodopsin", The Journal of Biological Chemistry 278(42):40493-40502.
Kocsis et al., (1982) "Regenerating Mammalian Nerve Fibres: Changes in Action Potential Waveform and Firing Characteristics Following Blockage of Potassium Conductance", Proc. R. Soc. Lond. vol. B Biol Sci 217(1206):77-87.
Kokel et al., (2013) "Photochemical Activation of TRPA1 Channels in Neurons and Animals", Nat Chem Biol 9(4):257-263.
Kravitz et al., (2010) "Regulation of Parkinsonian Motor Behaviours by Optogenetic Control of Basal Ganglia Circuitry", Nature 466(622):8 pages.
Kugler et al., (2001) "Neuron-Specific Expression of Therapeutic Proteins: Evaluation of Different Cellular Promoters in Recombinant Adenoviral Vectors", Molecular and Cellular Neuroscience 17:78-96.
Kuhlman et al., (2008) "High-Resolution Labeling and Functional Manipulation of Specific Neuron Types in Mouse Brain by Cre-Activated Viral Gene Expression", PLoS One e2005,3(4):1-11.
Kunkler et al., (2005) "Optical Current Source Density Analysis in Hippocampal Organotypic Culture Shows that Spreading Depression Occurs with Uniquely Reversing Current", The Journal of Neuroscience, 25(15):3952-3961.
Lalumiere (2011) "A New Technique for Controlling the Brain: Optogenetics and its Potential for use in Research and the Clinic", Brain Stimulation 4:1-6.
Lammel et al., (2012) "Input-Specific Control of Reward and Aversion in the Ventral Tegmental Area", Nature 491(7423):212-217.
Landy (1993) "Mechanistic and Structural Complexity in the Site-Specific Recombination Pathways of Int and FLP", Current Opinion in Genetics and Development 3:699-707.
Lanyi et al., (1990) "The Primary Structure of a Halorhodopsin from Natronobacterium Pharaonis", Journal of Biological Chemistry 265(3):1253-1260.
Lee et al., (2000) "Sterotactic Injection of Adenoviral Vectors that Target Gene Expression to Specific Pituitary Cell Types: Implications for Gene Therapy", Neurosurgery 46(6):1461-1469.
Lee et al., (2003) "Potassium Channel Gene Therapy Can Prevent Neuron Death Resulting from Necrotic and Apoptotic Insults", Journal of Neurochemistry 85:1079-1088.
Levitan et al., (2000) "Surface Expression of Kv1 Voltage-Gated K+ Channels is Governed by a C-terminal Motif", Trends Cardiovasc. Med.10(7):317-320.
Li et al., (2005) "Fast Noninvasive Activation and Inhibition of Neural and Network Activity by Vertebrate Rhodopsin and Green Algae Channelrhodopsin", PNAS 102(49):17816-17821.
Li et al., (2000) "Surface Expression of Kv1 Channels is Governed by a C-Terminal Motif", J. Bioi. Chem. 275(16):11597-11602.
Li et al., (2014) "Role of a Helix B Lysine Residue in the Photoactive Site in Channelrhodopsins", Biophysical Journal 106:1607-1617.
Li et al., (2014) "A Method for Activation of Endogenous Acid-sensing Ion Channel 1a (ASIC1a) in the Nervous System with High Spatial and Temporal Precision", The Journal of Biological Chemistry 289(22):15441-15448.
Lim et al., (2000) "A Novel Targeting Signal for Proximal Clustering of the Kv2.1K+ Channel in Hippocampal Neurons", Neuron 25:385-397.
Lima et al., (2005) "Remote Control of Behavior through Genetically Targeted Photostimulation of Neurons", Cell 121:141-152.
Liman et al., (1992) "Subunit Stoichiometry of a Mammalian K+ Channel Determined by Construction of Multimeric cDNAs", Neuron 9:861-871.
Lin (2010) "A User's Guide to Channelrhodopsin Variants: Features, Limitations and Future Developments", Exp Physiol 96(1):19-25.
Lin et al., (2009) "Characterization of Engineered Channelrhodopsin Variants with Improved Properties and Kinetics", Biophysical Journal 96(5):1803-1814.
Lin et al., (2010) "Study of the Circuitry of Nucleus Accumbens and its Effect on Addiction by Optogenetic Methods: 964", Neurosurgery 67(2):557.
Liske et al., (2013) "Optical Inhibition of Motor Nerve and Muscle Activity In Vivo", Muscle Nerve 47(6):916-21.
Liu et al., (2010) "Optogenetics 3.0", Cell 141(1):22-24.
Llewellyn et al., (2010) "Orderly Recruitment of Motor Units under Optical Control In Vivo", Nat Med. 16(10):1161-5.
Loetterle et al., (1975) "Cerebellar Stimulation: Pacing the Brain", American Journal of Nursing 75(6):958-960.
Lonnerberg et al., (1995) "Regulatory Region in Choline Acetyltransferase Gene Directs Developmental and Tissue-Specific Expression in Transgenic Mice", Proc. Natl. Acad. Sci. USA 92(9):4046-4050.
Louis et al., (1997) "Cloning and Sequencing of the Cellular-Viral Junctions from the Human Adenovirus Type 5 Transformed 293 Cell Line", Virology 233:423-429.

(56) References Cited

OTHER PUBLICATIONS

Luecke et al., (1999) "Structural Changes in Bacteriorhodopsin During Ion Transport at 2 Angstrom Resolution", Science 286:255-260.
Luo et al., (2000) "Synthetic DNA Delivery Systems", Nature Biotechnology 18:33-37.
Lyznik et al., (1996) "FLP-Mediated Recombination of FRT Sites in the Maize Genome", Nucleic Acids Research 24(19):3784-3789.
Ma et al., (2001) "Role of ER Export Signals in Controlling Surface Potassium Channel Numbers", Science 291:316-319.
Maestripieri et al., (1992) "A Modest Proposal: Displacement Activities as an Indicator of Emotions in Primates", Anim. Behav. 44:967-979.
Malin et al., (2007) "Involvement of the Rostral Anterior Cingulate Cortex in Consolidation of Inhibitory Avoidance Memory: Interaction with the Basolateral Amygdala", Neurobiol Learn Mem. 87(2):295-302.
Mancuso et al., (2010) "Optogenetic Probing of Functional Brain Circuitry", Experimental Physiology 96. 1:26-33.
Mann et al., (2005) "Perisomatic Feedback Inhibition Underlies Cholinergically Induced Fast Network Oscillations in the Rat Hippocampus in Vitro", Neuron 45(1):105-117.
Mann (2011) "Synapses", The Nervous System in Action Chapter 13 http://michaeldmann.net/mann13.html (downloaded Apr. 2014).
Marin et al., (2000) "The Amino Terminus of the Fourth Cytoplasmic Loop of Rhodopsin Modulates Rhodopsin-Transduction Interaction", The Journal of Biological Chemistry 275:1930-1936.
Masaki et al., (1996) "β2-Adrenergic Receptor Regulation of the Cardiac L-Type Ca2+ Channel Coexpressed in a Fibroblast Cell Line", Receptor 5:219-231.
Matsuda (2009) "Bed Nucleus of Stria Terminalis (BNST)", Benshi Seishin Igaku Molecular Psychiatric Medicine 9(3):46-49.
Mattis et al., (2011) "Principles for Applying Optogenetic Tools Derived from Direct Comparative Analysis of Microbial Opsins", Nat Methods 9(2):159-172.
Mattson (2000) "Apoptosis in Neurodegenerative Disorders", Nature Reviews 1:120-129.
Mayberg et al., (2008) "Deep Brain Stimulation for Treatment-Resistant Depression", Focus VI(1):143-154.
Mayford et al., (1996) "Control of Memory Formation through Regulated Expression of CaMKII Transgene", Science 274(5293):1678-1683.
McAllister (2000) "Cellular and Molecular Mechanisms of Dendrite Growth", Cereb Cortex 10(10):963-973.
McKnight (1982) "Functional Relationships between Transcriptional Control Signals of the Thymidine Kinase Gene of Herpes Simplex Virus", Cell 31:355-365.
Melyan et al., (2005) "Addition of Human Melanopsin Renders Mammalian Cells Photoresponsive", Nature 433:741-745.
Mermelstein et al., (2000) "Critical Dependence of cAMP Response Element-Binding Protein Phosphorylation on L-Type Calcium Channels Supports a Selective Response to EPSPs in Preference to Action Potentials", The Journal of Neuroscience 20(1):266-273.
Meyer et al., (2001) "High Density Interconnects and Flexible Hybrid Assemblies for Active Biomedical Implants," IEEE Transactions on Advanced Packaging 24(3):366-372.
Milella et al., (2010) "Opposite Roles of Dopamine and Orexin in Quinpirole-Induced Excessive Drinking: A Rat Model of Psychotic Polydipsia", Psychopharmacology 211:355-366.
Monje et al., (2002) "Irradiation Induces Neural Precursor-Cell Dysfunction", Natural Medicine 8(9):955-962.
Morelli et al., (1999) "Neuronal and Glial Cell Type-Specific Promoters within Adenovirus Recombinants Restrict the Expression of the Apoptosis-Inducing Molecule Fas Ligand to Predetermined Brain Cell Types, and Abolish Peripheral Liver Toxicity", Journal of General Virology 80:571-583.
Mortensen et al., (1997) "Selection of Transfected Mammalian Cells", Supplement 86, Current Protocols in Molecular Biology 9.5.1-09.5.19.
Mourot et al., (2012) "Rapid Optical Control of Nociception with an Ion Channel Photoswitch", Nat Methods 9(4):396-402.
Mueller et al., (2008) "Clinical Gene Therapy Using Recombinant Adeno-Associated Virus Vectors", Gene Therapy 15:858-863.
Mullins et al., (1989) "Expression of the DBA/2J Ren-2 Gene in the Adrenal Gland of Transgenic Mice", EMBO 8:4065-4072.
Mullins et al., (1990) "Fulminant Hypertension in Transgenic Rats Harbouring the Mouse Ren-2 Gene", Nature 344:541-544.
Nacher et al., (2003) "NMDA Receptor Antagonist Treatment Increases the Production of New Neurons in the Aged Rat Hippocampus", Neurobiology of Aging 24(2):273-84.
Nagel et al., (1995) "Functional Expression of Bacteriorhodopsin in Oocytes Allows Direct Measurement of Voltage Dependence of Light Induced H+ Pumping", FEBS Letters 377:263266.
Nagel et al., (2002) "Channelrhodopsin-I: A Light-Gated Proton Channel in Green Algae", Science 296:2395-2398.
Nagel et al., (2003) "Channelrhodopsin-2, a Directly Light-Gated Cation-Selective Membrane Channel", PNAS 100(24):13940-13945.
Nakagami et al., (1997) "Optical Recording of Trisynaptic Pathway in Rat Hippocampal Slices with a Voltage-Sensitive Dye", Neuroscience (81)1:1-8.
Naqvi et al., (2007) "Damage to the Insula Disrupts Addiction to Cigarette Smoking", Science 315:531-534.
Natochin et al., (2006) "Probing Rhodopsin-Transducin Interaction using *Drosophila* Rh1-Bovine Rhodopsin Chimeras", Vision Res. 46(27):4575-4581.
Nelson et al., (2009) "Non-Human Primates: Model Animals for Developmental Psychopathology", Neuropsychopharmacology 34(1):90-105.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Nieh et al., (2012) "Optogenetic Dissection of Neural Circuits Underlying Emotional Valence and Motivated Behaviors", Brain Research, E-pub 2012 1511:73-92.
Nirenberg et al., (1997) "The Light Response of Retinal Ganglion Cells is Truncated by a Displaced Amacrine Circuit", Neuron 18:637-650.
No Authors Listed (1996) "Two Bright New Faces in Gene Therapy", Nature Biotechnology 14:556.
Nonet (1999) "Visualization of Synaptic Specializations in Live C. Elegans with Synaptic Vesicle Protein-GFP Fusions", J. Neurosci. Methods 89:33-40.
Nunes-Duby et al., (1998) "Similarities and Differences among 105 Members of the Int Family of Site-Specific Recombinases", Nucleic Acids Research 26(2):391-406.
O'Gorman et al., (1991) "Recombinase-Mediated Gene Activation and Site-Specific Integration in Mammalian Cells", Science251(4999):1351-1355.
Olivares (2001) "Phage R4 Integrase Mediates Site-Specific Integration in Human Cells", Gene 278:167-176.
Ory et al., (1996) "A Stable Human-Derived Packaging Cell Line for Production of High Titer Retrovirus/Vesicular Stomatitis Virus G Pseudotypes", PNAS 93:11400-11406.
Packer et al., (2013) "Targeting Neurons and Photons for Optogenetics", Nature Neuroscience 16(7):805-815.
Palmer et al., (1999) "Fibroblast Growth Factor-2 Activates a Latent Neurogenic Program in Neural Stem Cells from Diverse Regions of the Adult CNS", The Journal of Neuroscience 19:8487-8497.
Palmer et al., (1997) "The Adult Rat Hippocampus Contains Primordial Neural Stem Cells", Molecular and Cellular Neuroscience 8:389-404.
Palu et al., (1999) "In Pursuit of New Developments for Gene Therapy of Human Diseases", Journal of Biotechnology 68:1-13.
Pan et al., (2005) "Functional Expression of a Directly Light-Gated Membrane Channel in Mammalian Retinal Neurons: A Potential Strategy for Restoring Light Sensitivity to the Retina After Photoreceptor Degeneration", Investigative Opthalmology & Visual Science 46 E-Abstract 4631. Abstract only.
Panda et al., (2005) "Illumination of the Melanopsin Signaling Pathway", Science 307:600-604.

(56) References Cited

OTHER PUBLICATIONS

Pandya et al., (2012) "Where in the Brain is Depression?", Curr. Psychiatry Rep. 14:634-642.
Pape et al., (2010) "Plastic Synaptic Networks of the Amygdala for the Acquisition, Expression, and Extinction of Conditioned Fear", Physiol Rev 90:419-463.
Paulhe et al., (2004) "Specific Endoplasmic Reticulum Export Signal Drives Transport of Stem Cell Factor (Kitl) to the Cell Surface", The Journal of Biological Chemistry 279(53):55545-55555.
Pear (1996) "Transient Transfection Methods for Preparation of High-Titer Retroviral Supernatants", Supplement 68, Current Protocols in Molecular Biology 9.1 1 .1-9.1 1 .1 8.
Peralvarez-Marin et al., (2007) "Inter-Helical Hydrogen Bonds are Essential Elements for Intra-Protein Signal Transduction: The Role of Asp115 in Bacteriorhodopsin Transport Function", J. Mol. Biol. 368:666-676.
Peterlin et al., (2000) "Optical Probing of Neuronal Circuits with Calcium Indicators", PNAS 97(7):3619-3624.
Petersen et al., (2003) "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions", The Journal of Neuroscience 23(3):1298-1309.
Petersen et al., (2011) "Functionally Independent Columns of Rat Somatosensory Barrel Cortex Revealed with Voltage-Sensitive Dye Imaging", J. of Neuroscience 21(21):8435-8446.
Petrecca et al., (2000) "Localization and Enhanced Current Density of the Kv4.2 Potassium Channel by Interaction with the Actin-Binding Protein Filamin", The Journal of Neuroscience 20(23):8736-8744.
Pettit et al., (1999) "Local Excitatory Circuits in the Intermediate Gray Layer of the Superior Colliculus", J Neurophysiol. 81(3):1424-1427.
Pfeifer et al., (2001) "Gene Therapy: Promises and Problems", Annu. Rev. Genomics Hum. Genet. 2:177-211.
Pinkham et al., (2008) "Neural Bases for Impaired Social Cognition in Schizophrenia and Autism Spectrum Disorders", Schizophrenia Research 99:164-175.
Potter (1996) "Transfection by Electroporation", Supplement 62, Current Protocols in Molecular Biology 9.3.1-9.3.6.
Pouille et al., (2004) "Routing of Spike Series by Dynamic Circuits in the Hippocampus", Nature 429:717-723.
Powell et al., (2006) "Schizophrenia-Relevant Behavioral Testing in Rodent Models: A Uniquely Human Disorder?", Biol. Psychiatry 59:1198-1207.
Prigge et al., (2010) "Functional Studies of Volvox Channelrhodopsin Chimeras", Biophysical Journal 98(3): Suppl. 1, 3694 Poster, 1 page.
Prigge et al., (2012) "Color-Tuned Channelrhodopsins for Multiwavelength Optogenetics", J. Biol. Chem. 287(38):31804-31812.
Qiu et al., (2005) "Induction of Photosensitivity by Heterologous Expression of Melanopsin", Nature 433:745-749.
Racaniello (2013) "How Many Viruses on Earth?", Virology Blog 6 pages; http://www.virology.ws/2013/09/06/how-many-viruses-on-earth/ (Sep. 6, 2013).
Ramalho et al., (2004) "Mouse Genetic Corneal Disease Resulting from Transgenic Insertional Mutagenesis", Br. J. Ophthalmol. 88(3):428-432.
Rammes et al., (2000) "Synaptic Plasticity in the Basolateral Amygdala in Transgenic Mice Expressing Dominant-Negative cAMP Response Element-Binding Protein (CREB) in Forebrain", Eur J. Neurosci. 12(7): 2534-2546.
Randic et al., (1993) "Long-Term Potentiation and Long-Term Depression of Primary Afferent Neurotransmission in the Rat Spinal Cord", Journal of Neuroscience 13(12):5228-5241.
Raper et al., (2003) "Fatal Systemic Inflammatory Response Syndrome in a Ornithine Transcarbamylase Deficient Patient Following Adenoviral Gene Transfer", Mol. Genet. Metab. 80(1-2):148-158.
Rathnasingham et al., (2004) "Characterization of Implantable Microfabricated Fluid Delivery Devices", IEEE Transactions on Biomedical Engineering 51(1):138-145.
Reeves et al., (2002) "Structure and Function in Rhodosin: A Tetracycline-Inducible System in Stable Mammalian Cell Lines for High-Level Expression of Opsin Mutants", PNAS 99(21):13413-13418.
Rein and Deussing (2012) "The Optogenetic (R)evolution", Mol. Genet. Genomics 287(2):95-109.
Remy et al., (2005) "Depression in Parkinson's Disease: Loss of Dopamine and Noradrenaline Innervation in the Limbic System", Brain 128(Pt 6):1314-1322.
Ristevski (2005) "Making Better Transgenic Models: Conditional, Temporal, and Spatial Approaches", Molecular Biotechnology 29(2):153-163.
Ritter et al., (2008) "Monitoring Light-Induced Structural Changes of Channelrhodopsin-2 by UV-Visible and Fourier Transform Infrared Spectroscopy", The Journal of Biological Chemistry 283(50):35033-35041.
Rivera et al., (2002) "BDNF-Induced TrkB Activation Down-Regulates the K+-Cl-Cotransporter KCC2 and Impairs Neuronal Cl-Extrusion", The Journal of Cell Biology 159:747-752.
Rogers et al., (2006) "Effects of Ventral and Dorsal CA1 Subregional Lesions on Trace Fear Conditioning", Neurobiology of Learning and Memory 86:72-81.
Rosenkranz et al., (2003) "The Prefrontal Cortex Regulates Lateral Amygdala Neuronal Plasticity and Responses to Previously Conditioned Stimuli", J. Neurosci. 23(35):11054-11064.
Rousche et al., (2001) "Flexible Polyimide-Based Intracortical Electrode Arrays with Bioactive Capability", IEEE Transactions on Biomedical Engineering 48(3):361-371.
Rubinson et at., (2003) "A Lentivirus-Based System to Functionally Silence Genes in Primary Mammalian Cells, Stem Cells and Transgenic Mice by RNA Interference", Nature Genetics 33:401-406.
Rudiger et at., (1997) "Specific Arginine and Threonine Residues Control Anion Binding and Transport in the Light-Driven Chloride Pump Halorhodopsin", The EMBO Journal 16(13):3813-3821.
Saiki et al., (2018) "Aldehyde Dehydrogenase 3A1 Activation Prevents Radiation-Induced Xerostomia by Protecting Salivary Stem Cells from Toxic Aldehydes", PNAS 115(115):6279-6284.
Salzman et al., (1990) "Cortical Microstimulation Influences Perceptual Judgements of Motion Direction", Nature 346:174-177.
Samuelson (2011) "Post-Traumatic Stress Disorder and Declarative Memory Functioning: A Review", Dialogues in Clinical Neuroscience 13(3):346-351.
Santana et al., (2012) "Can Zebrafish Be Used as Animal Model to Study Alzheimer's Disease?", Am. J. Neurodegener. Dis. 1(1):32-48.
Sato et al., (2005) "Role of Anion-Binding Sites in Cytoplasmic and Extracellular Channels of *Natronomonas pharaonis* Halorhodopsin", Biochemistry 44:4775-4784.
Sauer (1994) "Site-Specific Recombination: Developments and Applications", Current Opinion in Biotechnology 5(5):521-527.
Schiff et al., (2007) "Behavioral Improvements with Thalamic Stimulation after Severe Traumatic Brain Injury", Nature 448:600-604.
Schlaepfer et al., (2008) "Deep Brain Stimulation to Reward Circuitry Alleviates Anhedonia in Refractory Major Depression", Neuropsychopharmacology 33:368-377.
Schroll et al., (2006) "Light-Induced Activation of Distinct Modulatory Neurons Triggers Appetitive or Aversive Learning in *Drosophila larvae*", Current Biology 16(17):1741-1747.
Schuster et al., (2014) "Biodistribution of Adeno-Associated Virus Serotype 9 (AAV9) Vector after Intrathecal and Intravenous Delivery in Mouse", Frontiers in Neuroanatomy 8, Article 42:1-41.
Sclimenti et al., (2001) "Directed Evolution of a Recombinase for Improved Genomic Integration at a Native Human Sequence", Nucleic Acids Research 29(24):5044-5051.
Sheikh et al., (2013) "Neurodegenerative Diseases: Multifactorial Conformational Diseases and Their Therapeutic Interventions", Journal of Neurodegenerative Diseases Article ID 563481:1-8.

(56) References Cited

OTHER PUBLICATIONS

Shepherd et al., (2003) "Circuit Analysis of Experience-Dependent Plasticity in the Developing Rat Barrel Cortex", Neuron 38: 277-289.
Shibasaki et al., (2007) "Effects of Body Temperature on Neural Activity in the Hippocampus: Regulation of Resting Membrane Potentials by Transient Receptor Potential Vanilloid 4", The Journal of Neuroscience 27(7):1566-1575.
Shimizu et al., (2000) "NMDA Receptor-Dependent Synaptic Reinforcement as a Crucial Process for Memory Consolidation", Science 290:1170-1174.
Shoji et al., (2004) "Current Status of Delivery Systems to Improve Target Efficacy of Oligonucleotides", Current Pharmaceutical Design 10:785-796.
Sigmund (2000) "Viewpoint: Are Studies in Genetically Altered Mice Out of Control?", Arterioscler Thromb Vasc Biol. 20(6):1425-1429.
Silver et al., (1984) "Amino Terminus of the Yeast GAL4 Gene Product is Sufficient for Nuclear Localization", PNAS 81(19):5951-5955.
Simmons et al., (2008) "Localization and Function of NK3 Subtype Tachykinin Receptors of Layer Pyramidal Neurons of the Guinea-Pig Medial Prefrontal Cortex", Neuroscience 156(4):987-994.
Sineshchekov et al., (2002) "Two Rhodopsins Mediate Phototaxis to Low and High Intensity Light in Chlamydomas Reinhardtil", PNAS 99(13):8689-8694.
Sineshchekov et al., (2013) "Intramolecular Proton Transfer in Channelrhodopsins", Biophysical Journal 104(4):807-817.
Singer et al., (2002) "Elevated Intrasynaptic Dopamine Release in Tourette's Syndrome Measured by PET", American Journal of Psychiatry 159:1329-1336.
Singer (2009) "Light Switch for Bladder Control", Technology Review; pp. 1-2.
Skolnick et al., (2000) "From Genes to Protein Structure and Function: Novel Applications of Computational Approaches in the Genomic Era", Trends Biotechnol 18(1):34-39.
Slamovits et al., (2011) "A Bacterial Proteorhodopsin Proton Pump in Marie Eukaryotes", Nature Comm 2:183.
Slimko et al., (2002) "Selective Electrical Silencing of Mammalian Neurons In Vitro by the use of Invertebrate Ligand-Gated Chloride Channels", The Journal of Neuroscience 22(17):7373-7379.
Smith et al., (2002) "Diversity in the Serine Recombinases", Molecular Microbiology 44(2):299-307.
Smith et al., (2007) "Proton Binding Sites Involved in the Activation of Acid-Sensing Ion Channel ASIC2a", Neuroscience Letters 426:12-17.
Sofuoglu et al., (2009) "Cholinergic Functioning in Stimulant Addiction: Implications for Medications Development", CNS Drugs 239 (11):939-952.
Sohal et al., (2009) "Parvalbumin Neurons and Gamma Rhythms Enhance Cortical Circuit Performance", Nature 459(7247):698-702.
Song et al., (2001) "Differential Effect of TEA on Long-Term Synaptic Modification in Hippocampal CA1 and Dentate Gyrus In Vitro", Neurobiology of Learning and Memory 76(3):375-387.
Song (2002) "Genes Responsible for Native Depolarization-Activated K+ Currents in Neurons", Neuroscience Research 42:7-14.
Soofiyani et al., (2013) "Gene Therapy, Early Promises, Subsequent Problems, and Recent Breakthroughs", Advanced Pharmaceutical Bulletin 3(2):249-255.
Stark et al., (1992) "Catalysis by Site-Specific Recombinases", Trends Genet. 8(12):432-439.
Steimer (2002) "The Biology of Fear- and Anxiety-Related Behaviors", Dialogues in Clinical Neuroscience 4(3):231-249.
Stockklausner et al., (2001) "A Sequence Motif Responsible for ER Export and Surface Expression of Kir2.0 Inward Rectifier K+ Channels", FEBS Letters 493:129-133.
Stoll et al., (2002) "Phage TP901-I Site-Specific Integrase Functions in Human Cells", Journal of Bacteriology 184(13):3657-3663.
Stonehouse et al., (2003) "Caffeine Regulates Neuronal Expression of the Dopamine 2 Receptor Gene", Molecular Pharmacology 64(6):1463-1473.
Stuber (2010) "Dissecting the Neural Circuitry of Addiction and Psychiatric Disease with Optogenetics", Neuropsychopharmacology 35(1):341-342.
Suzuki et al., (2008) "Stable Transgene Expression from HSV Amplicon Vectors in the Brain: Potential Involvement of Immunoregulatory Signals", Molecular Therapy 16(10):1727-1736.
Swanson (2009) "Lights, Opsins, Action! Optogenetics Brings Complex Neuronal Circuits into Sharper Focus", The Dana Foundation, [URL:http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi et al., (1992) "Diversion of the Sign of Phototaxis in a *Chlamydomonas reinhardtii* Mutant Incorporated with Retinal and Its Analogs", FEBS Letters 314(3): 275-279.
Takahashi et al., (2006) "Induction of Pluripotent Stem Cells from Mouse Embryonic and Adult Fibroblast Cultures by Defined Factors", Cell 126:663-676.
Tam et al., (2000) "Identification of an Outer Segment Targeting Signal in the COOH Terminus of Rhodopsin Using Transgenic *Xenopus laevis*", The Journal of Cell Biology 151(7):1369-1380.
Tamai (2004) "Progress in Pathogenesis and Therapeutic Research in Retinitis Pigmentosa and Age Related Macular Degeneration", Nippon Ganka Gakkai Zasshi 108(12):750-769.
Tatarkiewicz et al., (1999) "Reversal of Hyperglycemia in Mice After Subcutaneous Transplantation of Macroencapsulated Islets", Transplantation 67(5):665-671.
Taurog et al., (1988) "HLA-B27 in Inbred and Non-Inbred Transgenic Mice", J. Immunol. 141 :4020-4023.
Thomas et al., (2003) "Progress and Problems with the Use of Viral Vectors for Gene", Nat. Rev. Genet. 4(5):346-358.
Tomita et al., (2009) "Visual Properties of Transgenic Rats Harboring the Channelrhodopsin-2 Gene Regulated by the Thy-1.2 Promoter", PLoS One 4(11):13 pages.
Tønnesen et al., (2009) "Optogenetic Control of Epileptiform Activity", PNAS 106(29):12162-12167.
Tottene et al., (2002) "Familial Hemiplegic Migraine Mutations Increase $Ca^{2+}$ Influx Through Single Human Cav2.1 Current Density in Neurons", PNAS USA 99(20):13284-13289.
Towne et al., (2010) "Efficient Transduction of Non-Human Primate Motor Neurons after Intramuscular Delivery of Recombinant AAV Serotype 6", Gene Ther. 17(1):141-146.
Towne et al., (2013) "Optogenetic Control of Targeted Peripheral Axons in Freely Moving Animals", PLoS One 8(8):e72691.
Towne et al., (2009) "Recombinant Adeno-Associated Virus Serotype 6 (rAAV2/6)-Mediated Gene Transfer to Nociceptive Neurons through Different Routes of Delivery", Mol Pain 5:52.
Tsai et al., (2009) "Phasic Firing in Dopaminergic Neurons in Sufficient for Behavioral Conditioning", Science 324:1080-1084.
Tsau et al., (1994) "Distributed Aspects of the Response to Siphon Touch in *Aplysia*: Spread of Stimulus Information and Cross-Correlation Analysis", The Journal of Neuroscience 14(7):4167-4184.
Tsuchida (1989) "Nervous Control of Micturition", The Japanese Journal of Urology 80(9):1257-1277.
Tsunoda & Hegemann (2009) "Glu 87 of Channelrhodopsin-1 Causes pH-Dependent Color Tuning and Fast Photocurrent Inactivation", Photochemistry and Photobiology 85(2):564-569.
Tye et. al., (2011) "Amygdala Circuitry Mediating Reversible and Bidirectional Control of Anxiety", Nature 471(7338):358-362.
Tye et. al., (2011) Supplementary Materials: "Amygdala Circuitry Mediating Reversible and Bidirectional Control of Anxiety", Nature 471(7338):358-362.
Tye et al., (2012) "Optogenetic Investigation of Neural Circuits Underlying Brain Disease in Animal Models", Nature Reviews Neuroscience 13(4):251-266.
Ulmanen et al., (1985) "Transcription and Translation of Foreign Genes in *Bacillus subtilis* by the Aid of a Secretion Vector", Journal of Bacteriology 162(1):176-182.

(56) References Cited

OTHER PUBLICATIONS

Uniprot Accession No. P02945, integrated into the database on Jul. 21, 1986.
Van Der Linden (2000) "Functional Brain Imaging and Pharmacotherapy in Social Phobia: Single Photon Emission Computed Tomography before and after Treatment with the Selective Serotonin Reuptake Inhibitor Citalopram", Prog Neuro-psychopharmacol Biot Psychiatry 24(3):419-438.
Vanin et al., (1997) "Development of High-Titer Retroviral Producer Cell Lines by using Cre-Mediated Recombination", Journal of Virology 71(10):7820-7826.
Varo et al., (1995) "Light-Driven Chloride Ion Transport by Halorhodopsin from Natronobacterium Pharaonis. 2. Chloride Release and Uptake, Protein Conformation Change, and Thermodynamics", Biochemistry 34(44):14500-14507.
Verma et al., (1997) "Gene Therapy—Promises, Problems and Prospects", Nature 389:239-242.
Vetter et al., (2005) "Development of a Microscale Implantable Neural Interface (MINI) Probe System", Proceedings of the 2005 IEEE, Engineering in Medicine and Biology 27th Annual Conference pp. 7341-7344.
Wagner (2007) "Noninvasive Human Brain Stimulation", Annual Rev. Biomed. Eng. 9:I9.I19.39.
Walker et al., (2009) "Selective Participation of the Bed Nucleus of the Stria Terminalis and CRF in Sustained Anxiety-Like Versus Phasic Fear-Like Responses", Prog Neuropsychopharmacol Bio Psychiatry, 13:33(8):1291-1308.
Wall (1996) "Transgenic Livestock: Progress and Prospects for the Future", Theriogenology 45:57-68.
Wang et al., (2007) "Direct-Current Nanogenerator Driven by Ultrasonic Waves", Science 316:102-105.
Wang et al., (2007) "High-Speed Mapping of Synaptic Connectivity using Photostimulation in Channelrhodopsin-2 Transgenic Mice", PNAS 104(19):8143-8148.
Wang et al., (2009) "Molecular Determinants Differentiating Photocurrent Properties of Two Channelrhodopsins from Chlamydomonas", The Journal of Biological Chemistry 284(9):5685-5696.
Wang et al., (2009) "Mrgprd-Expressing Polymodal Nociceptive Neurons Innervate Most Known Classes of Substantia Gelatinosa Neurons", J Neurosci 29(42):13202-13209.
Wang et al., (2009) "Laser-Evoked Synaptic Transmission in Cultured Hippocampal Neurons Expressing Channelrhodopsin-2 Delivered by Adeno-Associated Virus", Journal of Neuroscience Methods 183:165-175.
Wang et al., (2010) "Simultaneous Phase and Size Control of Upconversion Nanocrystals through Lanthanide Doping", Nature 463(7284):1061-1065.
Ward et al., (1986) "Construction and Characterisation of a Series of Multi-Copy Promoter-Probe Plasmid Vectors for *Streptomyces* using the Aminoglycoside Phosphotransferase Gene from Tn5 as Indicator", Mol. Gen. Genet. 203:468-478.
Watson et al., (2002) "Targeted Transduction Patterns in the Mouse Brain by Lentivirus Vectors Pseudotyped with VSV, Ebola, Mokola, LCMV, or MuLV Envelope Proteins", Molecular Therapy 5(5):528-537.
Weick et al., (2003) "Interactions with PDZ Proteins Are Required for L-Type Calcium Channels to Activate cAMP Response Element-Binding Protein-Dependent Gene Expression", The Journal of Neuroscience 23(8):3446-3456.
Weiss et al., (1998) "Galanin: A Significant Role in Depression?", Annals New York Academy of Sciences 863(1):364-382.
Williams et al., (2013) "From Optogenetic Technologies to Neuromodulation Therapies", Sci Transl Med. 5(177):177.
Winter et al., (2007) "Lesions of Dopaminergic Neurons in the Substantia Nigra Pars Compacta and in the Ventral Tegmental Area Enhance Depressive-Like Behavior in Rats", Behavioural Brain Research 184:133-141.
Witten et. al., (2010) "Cholinergic Interneurons Control Local Circuit Activity and Cocaine Conditioning", Science 330(6011):1677-1681.
Witten et. al., (2010) Supporting Online Material for: "Cholinergic Interneurons Control Local Circuit Activity and Cocaine Conditioning", Science 330:17 pages.
Witten et al., (2010) "Cholinergic Interneurons of the Nucleus Accumbens Control Local Circuit Activity and Reward Behavior", Society for Neuroscience Abstract Viewer and Itinerary Planner & 40th Annual Meeting of the Society-for-Neuroscience 40:2 pages.
Written opinion of PCT Application No. PCT/US2011/059383 (dated May 9, 2012).
Xiong et al., (1999) "Interregional Connectivity to Primary Motor Cortex Revealed using MRI Resting State Images", Hum Brain Mapp 8(2-3):151-156.
Yajima et al., (1984) "Effects of Bromazepam on Responses of Mucosal Blood Flow of the Gastrointestinal Tract and the Gastric Motility to Stimulation of the Amygdala and Hypothalamus in Conscious Cats", Folia Pharmacol. Japon 83(3):237-248. [English abstract translation].
Yamada (2003) "Neurobiological Aspects of Anxiety Disorders", The Japanese Journal of Psychiatry 8(6):525-535. [English translation of introduction and summary].
Yamazoe et al., (2006) "Efficient Generation of Dopaminergic Neurons from Mouse Embryonic Stem Cells Enclosed in Hollow Fibers", Biomaterials 27:4871-4880.
Yan et al., (2001) "Cloning and Characterization of a Human $\beta$, $\beta$-Carotene-15, 15'-Dioxygenase that is Highly Expressed in the Retinal Pigment Epithelium", Genomics 72:193-202.
Yizhar et al., (2011) "Optogenetics in Neural Systems", Neuron Primer 71(1):9-34.
Yizhar et al., (2011) "Neocortical Excitation/Inhibition Balance in Information Processing and Social Dysfunction", Nature 477:171-178; and Supplemental Materials; 41 pages.
Yoon et al., (2000) "A Micromachined Silicon Depth Probe for Multichannel Neural Recording", IEEE Transactions Biomedical Engineering 47(8):1082-1087.
Yoshimura et al., (2005) "Excitatory Cortical Neurons Form Fine-Scale Functional Networks", Nature 433:868-873.
Zacharias et al., (2000) "Recent Advances in Technology for Measuring and Manipulating Cell Signals", Current Opinion in Neurobiology 10:416-421.
Zemelman et al., (2002) "Selective Photostimulation of Genetically ChARGed Neurons", Neuron 33:15-22.
Zemelman et al., (2003) "Photochemical Gating of Heterologous Ion Channels: Remote Control over Genetically Designated Populations of Neurons", PNAS 100(3):1352-1357.
Zeng et al., (2015) "Activation of Acid-Sensing Ion Channels by Localized Proton Transient Reveals their Role in Proton Signaling", Scientific Reports 5:14 pages.
Zeng et al., (2012) "Proton Production, Regulation and Pathophysiological Roles in the Mammalian Brain", Neuroscience Bulletin 28(1):1-13.
Zhang (2007) "Multimodal Fast Optical Interrogation of Neural Circuitry", 446:633-641.
Zhang et al., (2006) "Channelrhodopsin-2 and Optical Control of Excitable Cells", Nature Methods 3(10):785-792.
Zhang et al., (2008) "Red-Shifted Optogenetic Excitation: A Tool for Fast Neural Control Derived from *Volvox carteri*", Nature Neurosciences 11(6):631-633.
Zhang, et al., (2011) "The Microbial Opsin Family of Optogenetic Tools", Cell 147(7):1146-1457.
Zhang et al., (2010) "Optogenetic Interrogation of Neural Circuits: Technology for Probing Mammalian Brain Structures", Nature Protocols 5(3):439-456.
Zhao et al., (2008) "Improved Expression of Halorhodopsin for Light-Induced Silencing of Neuronal Activity", Brain Cell Biology 36(1-4):141-154.
Zrenner (2002) "Will Retinal Implants Restore Vision?", Science 295(5557):1022-1025.
Zufferey et al., (1998) "Self-Inactivating Lentivirus Vector for Safe and Efficient In Vivo Gene Delivery", Journal of Virology 72(12):9873-9880.

\* cited by examiner

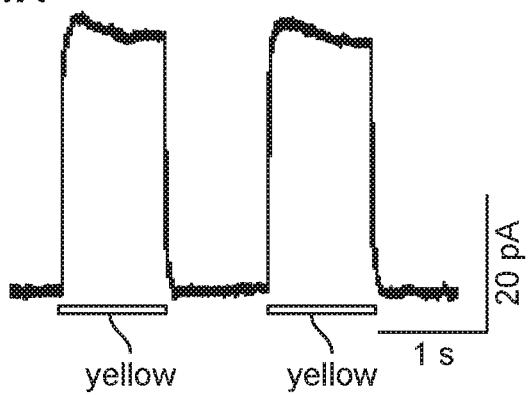
FIG. 1A
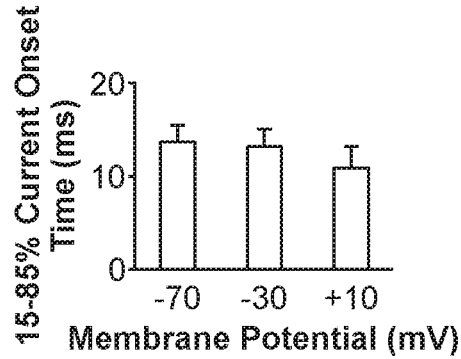
FIG. 1C
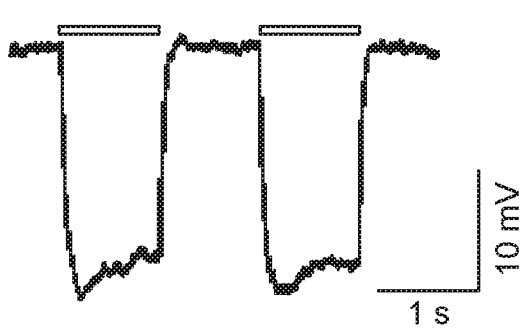
FIG. 1B
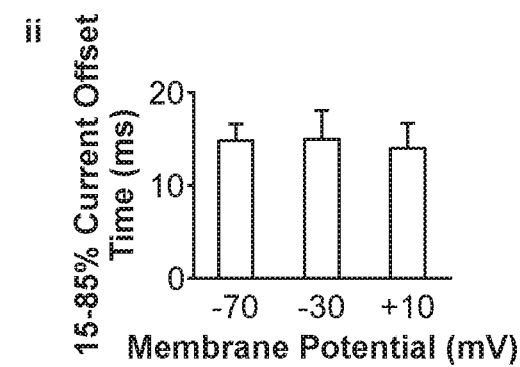
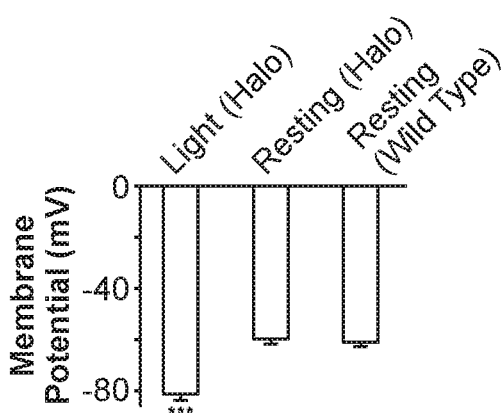
FIG. 1D
FIG. 1E
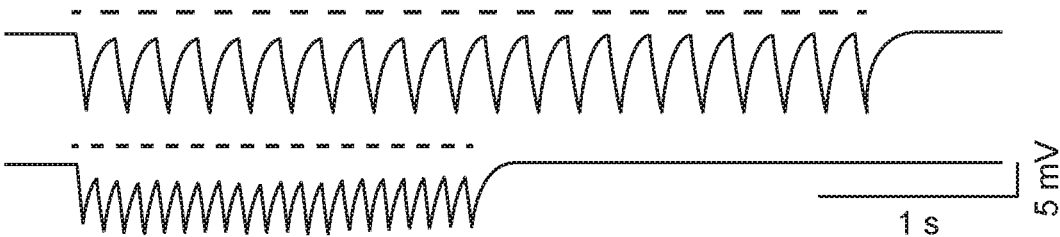

US 11,007,374 B2

SYSTEM FOR OPTICAL STIMULATION OF TARGET CELLS

RELATED PATENT DOCUMENTS

This application is a continuation of U.S. patent application Ser. No. 16/126,895, filed Sep. 10, 2018, now U.S. Pat. No. 10,369,378, which is a continuation of U.S. patent application Ser. No. 15/623,081, filed Jun. 14, 2017, now U.S. Pat. No. 10,105,551, which is a continuation of U.S. patent application Ser. No. 15/229,064, filed Aug. 4, 2016, which is a continuation of U.S. patent application Ser. No. 14/886,763, filed Oct. 19, 2015, which is a continuation of U.S. patent application Ser. No. 14/665,978, filed Mar. 23, 2015, now U.S. Pat. No. 9,187,745, which is a continuation of U.S. patent application Ser. No. 14/219,547, filed Mar. 19, 2014, which is a continuation of U.S. patent application Ser. No. 13/763,119, filed Feb. 8, 2013, now U.S. Pat. No. 8,864,805, which is a continuation of U.S. patent application Ser. No. 12/522,520, filed Jan. 8, 2010, now U.S. Pat. No. 8,398,692, which is a U.S. national phase filing under 35 U.S.C. § 371 of PCT/US2008/050745, filed Jan. 10, 2008, which application claims benefit under 35 U.S.C. § 119(e) both of U.S. Provisional Application No. 60/879,669 filed on Jan. 10, 2007 and entitled "Genetically-Targetable Optical Inactivation of Excitable Cells" and of U.S. Provisional Application No. 60/903,248 filed on Feb. 23, 2007 and entitled "Genetically-Targetable Optical Inactivation of Excitable Cells," each of which applications is herein fully incorporated by reference.

FIELD OF THE INVENTION

The present invention relates generally to systems and approaches for stimulating target cells, and more particularly, to using optics to dissuade stimulation-generated pulse trains.

BACKGROUND

Various efforts in neuroscience are directed towards determining whether neural activity in a specific brain region, or in a set of genetically-identified neurons, contributes to a particular neural computation, behavior, or neurological or psychiatric disorder. For centuries, insights have come from studies of human patients with specific lesions, as exemplified by Paul Broca's delineation in the 1860s of the eponymous brain area that, when dysfunctional, results in deficits of speech production. Many studies have used ablation or pharmacological shutdown of neurons or brain regions in animals, or careful analysis of patients, to parse out the physical substrates of normal and abnormal behavior. However, growing awareness that activity in multiple brain regions may be coordinated during performance of a behavior, or in a particular neural dysfunction, has raised the question of precisely when specific brain regions or neurons contribute. For example, a large number of in vivo recording studies have demonstrated, for many brain regions, that specific neurons can fire action potentials during precise intervals within a behavioral task. The intervals can last as little as a fraction of a second; it is possible that specific brain regions or neurons are required only at specific times in a task, not continuously. In humans, use of transcranial magnetic stimulation to disrupt the visual cortex has demonstrated that conscious perception requires intact cortical performance during temporal windows that last tens of milliseconds, occurring at precise times after visual stimulus presentation. Accordingly, a method for disrupting activity in targeted cell types for very precisely delimited periods of time (e.g., several milliseconds) could help answer a number of outstanding questions, and enable novel ones to be asked. For example, one question involves the identification of the precise brain regions, cell types, and activity patterns required at each phase (sensory, decision-making and motor) of a behavioral task. Another question involves, for a particular perception (e.g., feeling, decision, memory, or action) identifying the precise number of neurons that must be active within a certain region and how long the neurons are active. Another question involves the identification of the causal role of neural synchrony and precise spike timing in neural computation, plasticity, and pathological brain function. As memories are encoded, consolidated, and forgotten, it can be important to identifying how the critical neural loci of memory changes.

SUMMARY

The claimed invention is directed to photosensitive biomolecular structures and related methods. The present invention is exemplified in a number of implementations and applications, some of which are summarized below.

According to one example embodiment of the present invention, a method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIG. 1A shows sample outward currents elicited by two pulses of yellow light in a voltage-clamped neuron, consistent with an embodiment of the present invention;

FIG. 1B shows sample membrane voltage hyperpolarizations elicited by two pulses of yellow light, in a current-clamped neuron held at resting membrane potential, consistent with an embodiment of the present invention;

FIG. 1C shows Kinetic properties of yellow light-elicited, Halo-mediated currents from voltage-clamped neurons, consistent with an embodiment of the present invention;

FIG. 1D shows membrane potentials of neurons expressing Halo-GFP and exposed to yellow light, neurons expressing Halo-GFP but not exposed to any light, and neurons without transfection with Halo-GFP, consistent with an embodiment of the present invention;

FIG. 1E shows sample membrane hyperpolarizations induced by 5 Hz and 10 Hz trains of yellow light pulses, consistent with an embodiment of the present invention;

Figure 2A:
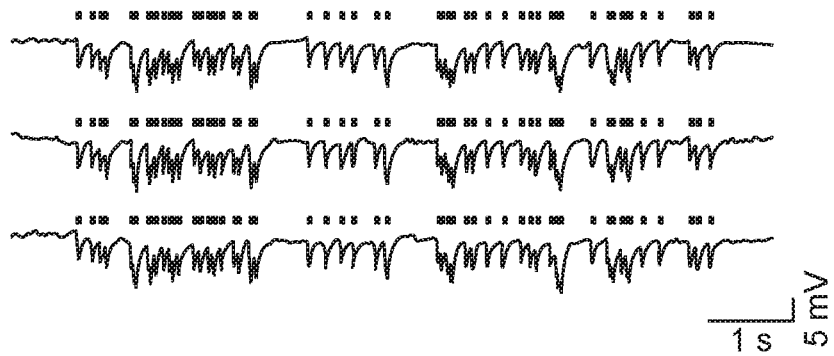
FIG. 2A shows three voltage traces of a current-clamped hippocampal neuron, exposed to a Poisson train of yellow light pulses, consistent with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of photosensitive biomolecular structures, and the invention has been found to be particularly suited for use in arrangements and methods dealing with neuron stimulation. While the present invention is not necessarily limited to such applications, various aspects of the invention may be appreciated through a discussion of various examples using this context.

The aspects of the present invention are directed to a technology that enables rapid neural inactivation and release from inactivation at the millisecond timescale, is safe and effective, has minimal effects on cellular physiology or survival, and requires no exogenous chemicals to be delivered. A specific embodiment of the invention involves a single-component protein capable of mediating light-induced inhibition, the mammalian codon-optimized version of the light-driven chloride pump halorhodopsin, from the archaebacterium Natronobacteriurn pharaonic (abbreviated Halo). Although such halobacteria are known to live in very high saline concentrations (e.g., >1 M), some wild-type halorhodopsins have been shown to preserve functionality at much lower chloride concentrations, even at levels comparable to those found in mammalian cerebrospinal fluid. Applications of the present invention involve the use of Halo to mediate optical inhibition of neuronal spiking in a physiologically accurate milieu, in response to pulses of somatically injected intracellular current (~300 PA), with temporal onset and offset of inhibition in the range of 10-15 milliseconds. Moreover, Halo can mediate naturalistic trains of inhibitory voltage changes at physiologically relevant frequencies, with minimal attenuation of voltage amplitude from pulse to pulse.

Aspects of an embodiment of the invention are also directed to a single neuron expressing both Halo and the blue-light driven cation channel Channelrhodopsin-2 (ChR2), neural inhibition and excitation are controlled at the millisecond timescale by pulses of yellow and blue light, respectively. In one instance, these channels provide the capability to create lesions of virally or transgenically targeted neural circuits over precise timescales, as well as neuroengineering interfaces for bi-directional control of excitable cell depolarization and hyperpolarization.

One embodiment of the present invention involves a designed fusion protein having the mammalian codon-optimized form of N. pharaonis halorhodopsin (Halo), with EGFP added in-frame at the C-terminus for ease of visualization. When expressed using the CaMKII promoter, which targets excitatory neurons of the forebrain, Halo-EGFP fluoresced brightly and appeared evenly distributed in the neuron. When exposed to ~10 m W/mm$^2$ yellow light (e.g., from a xenon lamp, filtered by a standard Texas red excitation filter (bandpass, 560±27.5 nm, Chroma), voltage-clamped hippocampal neurons expressing Halo can experience outward currents with rapid onset, stable steady-state, and abrupt shut-off with cessation of illumination. In some instances, no supplementation of the culture medium or the recording medium with the halorhodopsin cofactor all-trans retinal is necessary. This is believed to be due to levels of all-trans retinal naturally occurring in mammalian neurons in culture and in live brain that are high enough to enable type I opsins without chemical supplementation.

FIG. 1 shows the results of an experimental test of millisecond-timescale, yellow light-driven, neuronal hyperpolarization with Halo. A cultured hippocampal neuron expressing mammalian codon-optimized N. pharaonic halorhodopsin (Halo) fused to GFP under the CaMKII promoter is used.

FIG. 1A shows sample outward currents elicited by two 1-second pulses of yellow (560±27.5 nm) light (~10 mW/mm$^2$) in a voltage-clamped neuron held at −70 mV. Yellow bars in this and subsequent figures indicate the period of yellow light exposure.

FIG. 1C shows Kinetic properties of yellow light-elicited, Halo-mediated currents from voltage-clamped neurons. FIG. 1C$i$ shows 15-85% current onset time. FIG. 1C$ii$ shows 85-15% offset time. For each measurement, data is presented from neurons held at −70 mV (n=14 neurons), −30 mV (n=10), and +10 mV (n=10) (left to right). Bars represent mean±standard error of the mean (S.E.M.).

FIG. 1B shows sample membrane voltage hyperpolarizations elicited by two 1-second pulses of yellow light, in a current-clamped neuron held at resting membrane potential.

FIG. 1D shows membrane potentials of neurons expressing Halo-GFP and exposed to yellow light (left, n=14), expressing Halo-GFP but not exposed to any light (middle, n=11), and without transfection with Halo-GFP (right, n=8). *** denotes significant difference between the Halo-GFP+ light condition and each of the other two conditions (p<0.0001; Fisher's partial least-squares difference (PLSD) post hoc test after ANOVA).

FIG. 1E shows sample membrane hyperpolarizations induced by 5 Hz (top) and 10 Hz (bottom) trains of yellow light pulses, with light pulse durations of 50 ms (top) and 25 ms (bottom), respectively.

In related experimental tests, the light pulses elicited pulse amplitudes of 56.9±23.4 pA (mean±st. dev.; n=14 neurons). Repeating a 1-second pulse of yellow light twice, spaced by 1 second in darkness, resulted in identical pulse amplitudes each time (p>0.50, paired t-test), as shown in FIG. 1A.

This stable current amplitude appears to be consistent with what is known about the halorhodopsin photocycle. As befits a chloride pump, the current amplitude did not vary significantly with holding voltage (F=0.004, p>0.95, ANOVA with factor of holding voltage), nor did any measured kinetic parameters vary, such as the onset or offset times of the current pulses (F<0.6, p>0.55 for all comparisons, ANOVA; FIG. 1C). The onset and offset times of elicited currents were seen to be on the order ~10-15 ms at all holding voltages tested. This suggests that Halo is a viable candidate for ultratransient shutdown of spike trains (FIG. 1C$i$, 1C$ii$). When held in current clamp, hippocampal neurons underwent peak hyperpolarizations of −21.6±11.3 mV (mean±st. dev.; n=11 neurons) in response to pulses of yellow light, with no difference between the peak hyperpolarizations achieved by two pulses separated by a 1-second pause (p>0.85, paired t-test; FIG. 1B). These large voltage changes were relatively rapid, with onset and offset times of 68±57 and 73±39 ms, respectively. Thus, Halo has been shown to be capable of reliably mediating hyperpolarizations of significant magnitude, with fast onset and offset times at the beginning and end of light exposure.

Several control experiments were implemented to evaluate whether Halo has unanticipated side effects, such as altering basal cell physiology or increasing the propensity for cell death. First, the basal state of Halo-expressing neurons electrophysiologically was characterized when no light was present. When measured in darkness, no difference was seen between the resting potentials of neurons expressing Halo and those of neighboring neurons in the culture that were untransfected (p>0.20, n=11 Halo-positive cells, n=8 Halo-negative cells; FIG. 1D). This result suggests that basal neural activity would be little affected by the presence of Halo. On the other hand, Halo-expressing neurons illuminated with yellow light were significantly hyperpolarized, with respect to both Halo-expressing neurons in darkness and non-transfected cells (p<0.0001 for both of these comparisons, Fisher's partial least squares difference post hoc test after ANOVA (F=28.4, p<0.0001) with factor of experimental condition; FIG. 1D). An independent assay for unanticipated effects on cell health, the membrane-impermeant DNA stain ethidium homodimer-1 was used to detect the cell membrane breakdown accompanying cell death for one week in Halo-expressing cells. Little difference was found in the prevalence of cell death between Halo-positive and Halo-negative neurons: 16/308 (5.2%) non-transfected neurons counted, and 1/22 (4.5%) Halo-expressing neurons counted, were labeled by ethidium homodimer-1, indicating that Halo was not toxic over the course of the one-week experiment (x2=0.02, p>0.85).

In an effort to explore the uses Halo could present in the analysis and engineering of intact neural circuits, an experiment was performed to determine whether the fast response times of Halo could support naturalistic sequences of hyperpolarization events, in response to trains of brief pulses of yellow light.

FIG. 2 shows high-fidelity Halo-mediated naturalistic trains of inhibitory events. FIG. 2A shows three voltage traces of a current-clamped hippocampal neuron, exposed to a Poisson train of yellow light pulses. Each light pulse lasts 10 ms, and the Poisson train has a mean inter-pulse interval of $\lambda$=100 ms.

Figure 2B:
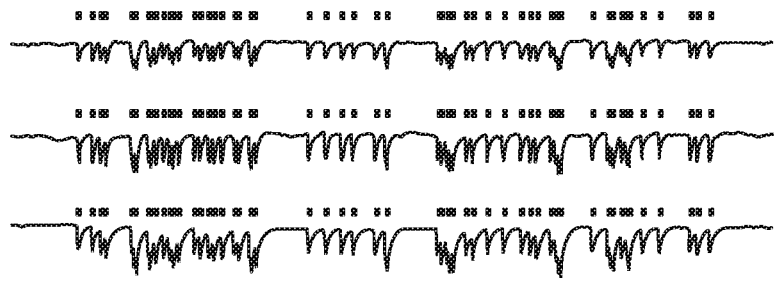
FIG. 2B shows voltage traces of three different current-clamped neurons exposed to the same Poisson train of light pulses (λ1=100 ms), consistent with an embodiment of the present invention.

FIG. 2B shows voltage traces of three different current-clamped neurons exposed to the same Poisson train of light pulses ($\lambda$=100 ms).

Figure 2C:
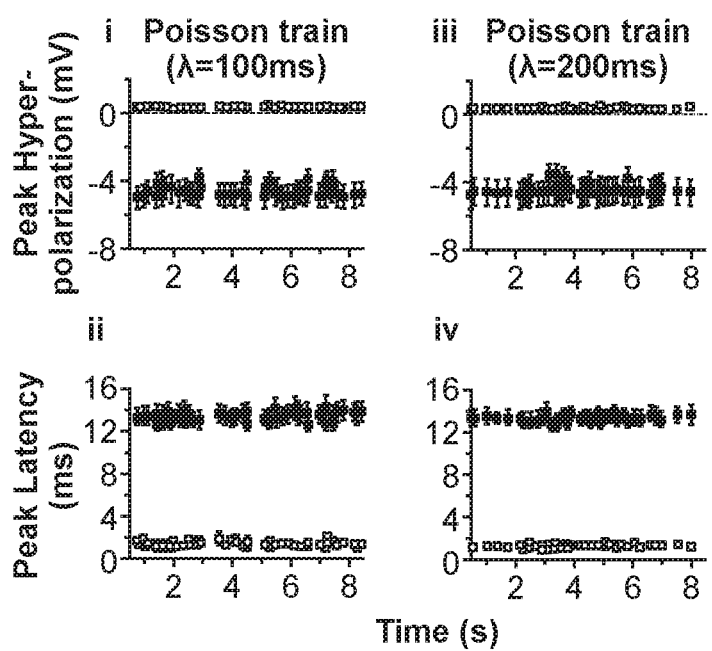
FIG. 2C shows properties of hyperpolarization events elicited by Poisson trains with various inter-pulse intervals, consistent with an embodiment of the present invention.

FIG. 2C shows properties of hyperpolarization events elicited by Poisson trains with inter-pulse interval $\lambda$=100 ms (i, ii) and $\lambda$=200 ms (iii, iv), plotted versus onset time of each light pulse. Plots (i) and (iii) show the peak of each hyperpolarization event, as well as the across-trials standard deviation of these amplitude values across ten trials. Plots (ii) and (iv) show the latency between the onset time of the light pulse and the time of the hyperpolarization peak, as well as the across-trials standard deviation of these timing values across ten trials. All plotted points are across-neuron mean±S.E.M. (n=5 neurons).

Figure 2D:
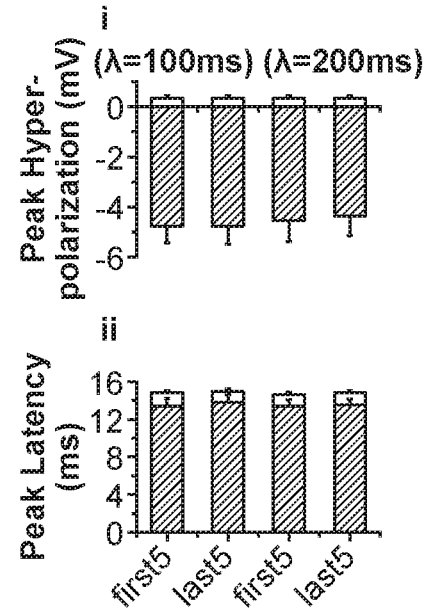
FIG. 2D shows a comparison of the peak hyperpolarization and the time-to-peak data at the beginning and end of the Poisson trains, for the neurons described in FIG. 2C, consistent with an embodiment of the present invention.

FIG. 2D shows a comparison of the peak hyperpolarization (i) and the time-to-peak (ii) data at the beginning (first 5) and end (last 5) of the $\lambda$=100 ms and $\lambda$=200 ms Poisson trains, for the n=5 neurons described in FIG. 2C. In (i): for each neuron, the average of the first 5 or last 5 hyperpolarization peaks or the across-trials standard deviation of these amplitude values was first computed, then the across-neuron mean±S.E.M. was plotted. In (ii): for each neuron, the average of the first 5 or last 5 times-to-peak or the across-trials standard deviation of these times-to-peak were first computed, then the across-neuron mean±S.E.M. was plotted.

FIG. 2A shows three traces of hyperpolarization events elicited in a single neuron, resulting from repeatedly playing back a Poisson train (mean inter-pulse interval, $\lambda$=100 ms, 59 pulses), of 10 ms-duration yellow light pulses, to simulate stochastic synaptic inhibitory input. FIG. 2B shows three such hyperpolarization traces, taken from different neurons. The variability of such trains was remarkably low in many regards—across ten repeated trials in a single cell, across multiple cells (n=5 neurons), and over time throughout a sustained train of 59 pulses (FIG. 2C, 2D). It was found that for hyperpolarizations elicited by 10 ms-duration light pulses during a $\lambda$=100 ms Poisson train, the mean amplitude was −4.56 mV (averaged across trials and neurons), but the trial-to-trial standard deviation of this amplitude was only 0.40 mV (averaged across neurons, FIG. 2C$i$ and FIG. 2D$i$). The trial-to-trial jitter of the time the hyperpolarization took to reach its peak value was also small, 1.27 ms (averaged across neurons, FIG. 2C$ii$ and FIG. 2D$ii$). The neuron-to-neuron variability of amplitude and timing was somewhat larger than the trial-to-trial variability, with standard deviations of 1.45 mV and 1.78 ms, respectively, but demonstrating that precise inhibitory control of a population of neurons could proceed with millivolt and millisecond resolution. Finally, the through-train sustainability of light-elicited voltage changes was quantitatively examined by comparing the amplitude mean and amplitude variability, and timing variability of the hyperpolarization events elicited by the first five light pulses to those of the last five light pulses in the train (FIGS. 2D$i$ and 2D$ii$, left side). Little or no difference was seen for any of these statistics between the beginning and end of a train (p>0.10 for all measures, t-test). Identical conclusions held for the $\lambda$=200 ms Poisson train with 46 pulses (FIGS. 2C$iii$ and 2C$iv$, and FIGS. 2D$i$ and 2D$ii$, right side). The high temporal and amplitude fidelity of Halo-mediated hyperpolarizations suggests uses for Halo in simulating inhibitory synaptic inputs, with great precision.

Figure 3A:
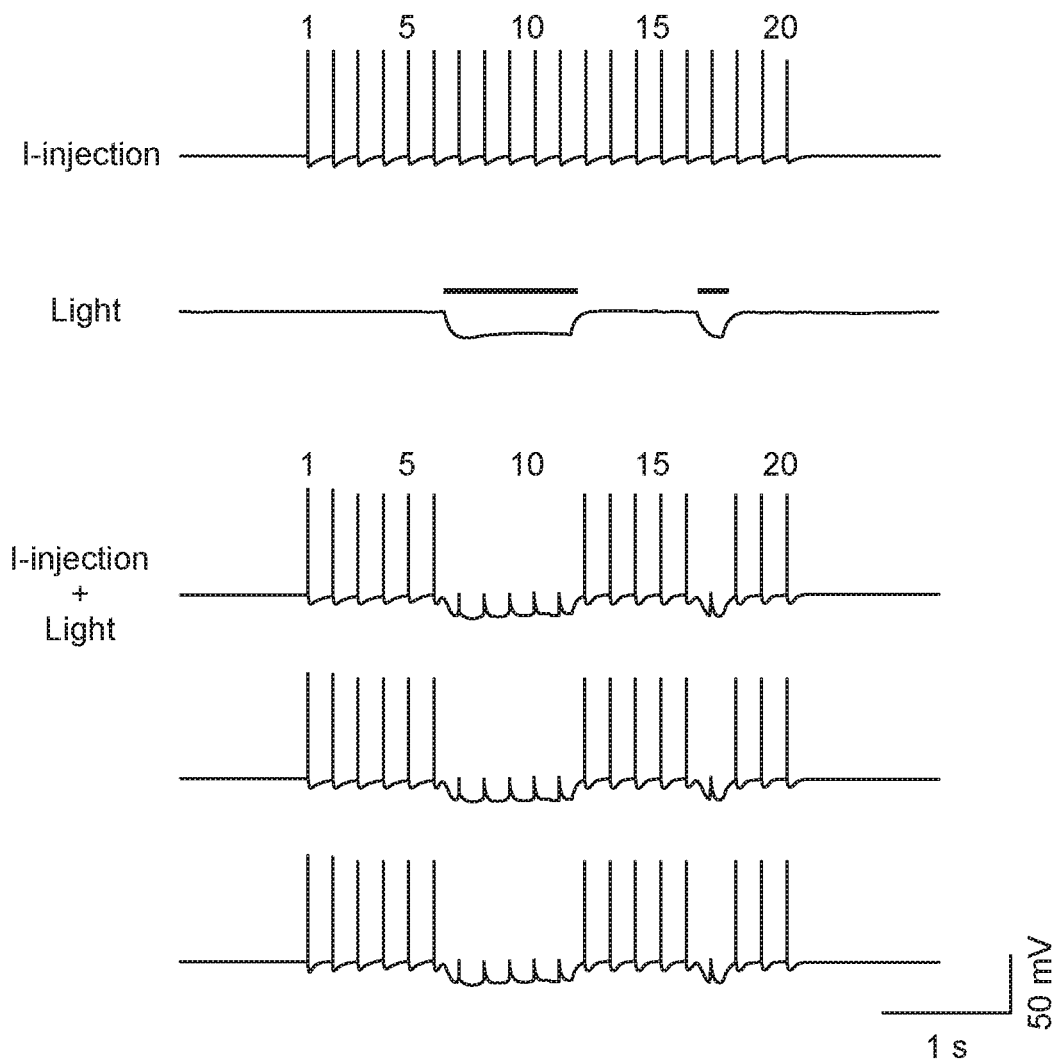
FIG. 3A shows a light-driven spike blockade, demonstrated for a single hippocampal neuron, consistent with an embodiment of the present invention.

FIG. 3 shows reliable and repeatable Halo-mediated neural inactivation, at single-spike temporal resolution. FIG. 3A shows a light-driven spike blockade, demonstrated for a single hippocampal neuron. At the top of FIG. 3A, labeled with "I-injection," neuronal firing of 20 spikes at 5 Hz are induced by pulsed somatic current injection (~300 pA, 4 ms). In the middle of FIG. 3A, labeled with "light," light membrane hyperpolarizations are induced by two periods of yellow light, timed so as to be capable of blocking spikes 7-11 and spike 17 out of the train of 20 spikes. At the bottom of FIG. 3A, labeled as "I-injection+Light", yellow light drives Halo to block neuron spiking (note significant reductions of spikes 7-11 and of spike 17), while leaving spikes elicited during periods of darkness largely intact.

Figure 3B:
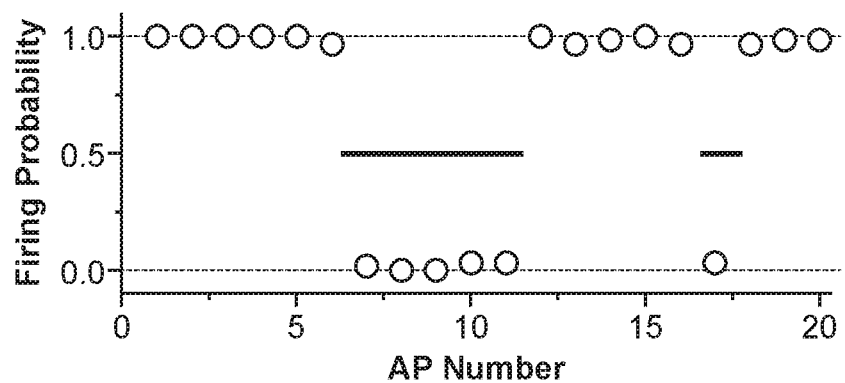
FIG. 3B shows population data (n=6 neurons) for light-driven, Halo-mediated spike blockade, consistent with an embodiment of the present invention.

FIG. 3B shows population data (n=6 neurons) for light-driven, Halo-mediated spike blockade, showing high spike probability during periods of darkness (spikes 1-6, 12-16, and 18-20), and low spike probability during periods of yellow-light illumination (spikes 7-11 and spike 17). Error bars are smaller than the points plotted.

Such experiment were implemented to analyze the ability of Halo to enable rapidly inducible and reversible silencing of neuron spiking. Such ability can be useful to enable time-resolved parsing of the precise neural substrates of behavior. Neurons were intracellularly injected with trains of somatic current pulses (~300 PA, lasting ~4 ms), causing them to fire action potentials at 5 Hz with 100% success rate (FIG. 3A, "I-injection"). Yellow-light pulses were scheduled to occur during the times when certain spikes (i.e., spikes 7-11 and 17) would occur during the somatic current injection protocol (FIG. 3A). The light pulses and the somatic current pulses were presented together (FIG. 3A, "I-injection+light", three trials shown). Spiking was effectively blocked during the periods of yellow-light exposure. The rapid onset and offset kinetics of Halo allowed the deletion of even single spikes. For instance, the second yellow-light pulse, timed for silencing just spike 17, was able to effectively eliminate spike 17 without affecting the firing of spikes 16 or 18 at all. The experiment was repeated five times on each of n=6 neurons (FIG. 3B). During periods when the yellow light was off, it was found that somatic current pulses elicited a spike 98.7% of the time. In contrast, during periods when the yellow light was on, somatic current pulses elicited a spike only 1.2% of the time. The second pulse of yellow light reduced the probability of firing spike 17 to 3.3%, whereas spikes 16 and 18 still fired 96.7% of the time, not significantly different from the spikes at the beginning of the train, before any light exposure at all ($X^2=1.02$, $p>0.30$). The temporal precision of Halo in silencing spikes therefore offers the possibility of creating ultra-transient (yet precise and effective) lesions of activity in targeted neurons.

A specific embodiment of the present invention includes the use of one member of the type I opsin family, Channelrhodopsin-2 (ChR2), which has received recent attention for its ability to drive neural excitation in response to pulses of blue light (centered around 470 nm). The ability to drive excitation and inhibition in the same neuron, using two different wavelengths of light, could enable answers to questions for which no current technology permits resolution. For example, synchronous neural activity has been correlated with higher-order functions, such as attention and abnormal patterns of neural synchrony that are associated with certain neurological and psychiatric disorders. The ability to drive a neuron with balanced but randomly varying excitation and inhibition may allow alteration of the precise timing of membrane voltage fluctuations, in principle permitting neural synchronization or desynchronization without any side effects, such as alteration of spike rate. This may open up new experiments in testing the causal role of neural synchrony in behavior and pathology.

Figure 4A:
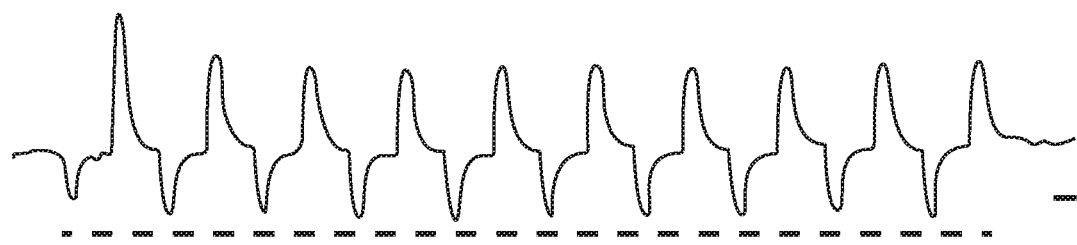
FIG. 4A shows responses of single neurons co-expressing Halo and ChR2, both under control of the CaMKII promoter, to rapidly-switched pulses of yellow and blue light, consistent with an embodiment of the present invention.
Figure 4B:
FIGS. 4B-4D show poisson trains of rapidly-alternating yellow and blue light pulses elicited rapidly-alternating hyperpolarizations and depolarizations in the same neuron, consistent with an embodiment of the present invention.
Figure 4C:
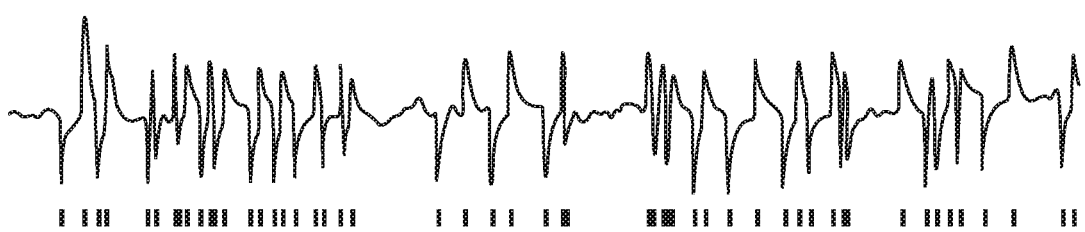
Figure 4D:
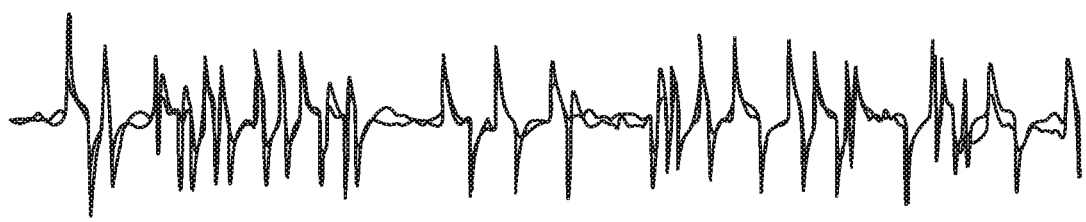

Single neurons co-expressing Halo and ChR2, both under control of the CaMKII promoter, were implemented to allow for response to rapidly-switched pulses of yellow and blue light with hyperpolarizations and depolarizations, respectively (FIG. 4A). Poisson trains ($\lambda=100$ ms) of rapidly-alternating yellow and blue light pulses elicited rapidly-alternating hyperpolarizations and depolarizations in the same neuron (FIG. 4B). In one experiment, the same Poisson train was played back twice with the first train beginning on a blue pulse (FIG. 4B) and the second train beginning on a yellow pulse, (FIG. 4C) so that in the second trace, depolarizations were converted into hyperpolarizations and vice versa. In principle, these traces should be quite similar, but with inverted voltage scale. Indeed, FIG. 4C shows an inverted trace superimposed over the trace in FIG. 4B. The degree of superposition suggests that this approach may indeed be a viable method for high-fidelity, bi-directional control of neural activity at the millisecond timescale (FIG. 4D).

The inhibition provided by Halo is strong enough to silence neurons firing spikes in response to significant intracellular somatic current injections (FIG. 3), yet the photocurrents can appear and disappear within 10-15 milliseconds of light onset and offset, respectively (FIG. 1). Furthermore, the amplitude and timing of responses is reliable from trial to trial, and the amplitude of the voltage changes induced by pulses of yellow light does not detectably run down over time (FIG. 2). The use of Halo can be particularly useful for a number of reasons. For example, the timescale of inducing of and subsequent release of voltage inhibition by Halo is relatively fast.

According to another embodiment of the present invention, Halo is used without ChR2. Millisecond pulses of light can be used with Halo-expressing cells to induce hyperpolarizations of several millivolts, and therefore, may be useful for simulating background or well-timed synaptic activity. Studying the function of not only specific cell types, but specific classes of inhibitory synapse, can be accomplished by creating fusion proteins in which Halo is targeted to specific locations where inhibitory synapses uniquely cluster, such as the axon initial segment.

The ability to functionally lesion brain regions or cell types in a rapidly reversible fashion opens up a large class of experiments in which specific neuron populations must be inactivated for precise, sub-second durations during a task. ChR2, another type I opsin which obligately requires all-trans-retinal for its function, has been shown to function in slices of mammalian brain tissue, or even in the central nervous system in vivo, without needing any chemical supplementation. Therefore, it is believed that no supplementation will be needed for Halo in the intact mammalian brain and in brain slice experiments. Other labs working on classical neural model organisms such as *Drosophila* and *C. elegans* have devised ways of delivering all-trans-retinal to the nervous systems of such animals in order to enable ChR2 function, and thus, it is likely that these retinal-delivery protocols would also work for enabling Halo function in these invertebrates.

The ability to study the causal role of neural synchrony in behavior, neural computation, and neural pathology may be a particularly significant role for ChR2 and Halo, working in concert. The newly-enabled power to drive both excitation and inhibition of genetically-targeted neurons with blue and yellow light seems to be particularly valuable for probing synchrony by utilizing multiple wavelengths to perform both excitation and inhibition in the same specimen. The ability to synchronize and desynchronize neurons by balanced, yet random, patterns of excitation and inhibition may open up new horizons into understanding the causal role of neural synchrony in brain function and disease, an area of longstanding, yet growing, interest.

Optical methods for altering neural circuit function have appeal in part because in principle they can use technology developed for brain imaging. The ability to use optical fibers to image deep neural circuits, for example, also enables the stimulation of deep brain structures. Two-photon excitation methods may prove valuable for driving opsin activities, up to 1 mm deep. Another key aspect of optical methods of neural control is the speed with which activation and inactivation can take place, since it is trivial to modulate light intensity at high speeds, faster than most physiologically relevant processes. Nevertheless, non-optical and chemical approaches will continue to find many powerful uses for reliable, enduring inhibition of specific brain circuits and cell types, especially when large regions of deep brain tissue are involved.

From a neuroengineering standpoint, optical prosthetics capable of inhibiting neural activity may present less-invasive strategies for treating disorders of neural hyperactivity. ChR2 has already proven to be well-tolerated in intact mammalian neural circuits for up to a year. If Halo gains a similar track record, it is possible that Halo-enabled prosthetics may open up new horizons in controlling disorders of excitable cells, such as epilepsy, depression, neuropathic pain, and cardiac hyperexcitability. In the immediate future, the ability to study the effects of well-timed neuron or circuit inactivation in animal models of disease will rapidly reveal new principles for selecting neural circuit targets for treatment of specific disorders. There are also implications of the use of Halo in biotechnological scenarios, such as high-throughput drug screening. Several proposals (and even commercially-available systems) exist for using electrical stimulation to activate excitable cells, thus facilitating the screening of depolarization-gated ion channels. The discovery of drugs that target hyperpolarization-activated channels, such as the family of channels mediating the hyperpolarization-activated cation currents I(h) and I(f), may be useful for identifying possible drugs for tackling problems such as absence seizures, bradycardia, and other disorders. An all-optical method for screening for such drugs, which uses light of one frequency to drive inhibition, and light of another frequency to observe changes in fluorescence of an ion-sensitive chemical or genetically encoded sensor, may revolutionize this process. Thus, Halo not only presents a number of unique features that enable effective, and rapidly inducible and reversible, inhibition to be applied to a number of neural circuit questions, but may open up new horizons in biotechnology as well.

An experimental hippocampal neuron culture, transfection, and survival assay was implemented according to the following methods. Hippocampal regions CA3-CAI of postnatal day 0 or day 1 Sprague-Dawley rats (Charles River) were isolated and treated with trypsin (1 mg/ml) for 12 minutes. Digestion was stopped by Hanks solution supplemented with 20% fetal bovine serum and trypsin inhibitor. Tissue was dissociated with silicone-coated Pasteur pipettes and centrifuged at 1000 rpm at 4° C. for 10 minutes. Dissociated neurons were plated on glass coverslips pre-coated with Matrigel (BD Biosciences) at a rough density of approximately two hippocampi per 24 coverslips. Neurons were transfected using a commercially available calcium phosphate transfection kit (Invitrogen), at 3-5 days in vitro. GFP fluorescence was used to identify successfully-transfected neurons, indicating a net transfection efficiency of ~7%. All images and electrophysiological recordings were made on 9-15 day-in-vitro neurons (approximately 4-10 days after transfection). Confocal images of transfected neurons were taken with a Zeiss LSM 510 confocal microscope. Cell death count was carried out on living cultures, seven days after transfection, by adding 4 μM ethidium homodimer-1 (Invitrogen) to the culture medium for 10 minutes at 37° C., then washing the cells with Tyrode's solution (see below). GFP-positive and negative neurons were counted for positive and negative ethidium fluorescence, in five regions on each of three coverslips for this viability assay.

An experiment regarding electrophysiology and optical methods was implemented according to the following methods. Whole cell patch clamp recording was made on 9-15 day-in-vitro neurons using a Multiclamp 700B amplifier, connected to a Digidata 1440 digitizer (Molecular Devices) attached to a PC running pClamp 10. During recording, neurons were bathed in Tyrode's solution containing (in mM) 138 NaCl, 2.4 KCl, 2 CaCl, 2 MgCl, 10 HEPES, 10 Glucose, 24 sucrose, 10 μM NBQX, 10 μM gabazine and 50 μM D-APV. Borosilicate glass (Warner) pipettes were filled with a solution containing (in mM) 130 K-Gluconate, 7 KCl, 2 NaCl, 1 MgCl2, 0.4 EGTA, 10 HEPES, 2 ATP-Mg, 0.3 GTP-Tris and 20 sucrose. Pipette resistance was ~6 M'Ω, and the access resistance was 10-25 M'Ω, which was monitored throughout the voltage-clamp recording. Resting membrane potential was 52-70 mV in current-clamp recording.

Photocurrents were first measured with pairs of 1-second long light pulses, separated by periods of darkness lasting 1 second, while holding neurons in voltage clamp at −70 mV, −30 mV and +10 mV to assay the properties of Halo. Light-induced membrane hyperpolarizations were induced by 1 second duration light pulses, separated by periods of 1 second darkness, in neurons current-clamped at resting membrane potential. Light pulse trains were synthesized by custom software written in MATLAB (Mathworks), and then played to the DG-4 light source through a digital-to-analog converter on the Digidata 1440. For the spike-blockade experiment, spikes were first induced via somatic current injection through the patch pipette. Most of the neurons patched easily fired action potentials with 100% probability, in response to ~300 pA current injections (4 ms duration). For each neuron, injected somatic current magnitudes guaranteed 100% firing rate of 20 spikes, at a rate of 5 Hz.

A DG-4 optical switch with 300-W xenon lamp (Sutter Instruments) was used to deliver all light pulses, for Halo or ChR2 activation. A Texas Red filter set (Chroma, excitation 560/55, diachronic 595LP, emission 645/75) was used to deliver yellow light to activate Halo. The same diachroic mirror was also used to deliver blue light, but with an excitation filter 480/40 in the DG-4, to allow ChR2 excitation. Note that the DC595LP dichroic mirror only reflects 35% of incident 460-500 nm light through the objective; custom-coated dichroics that reflect light all the way into the ultraviolet (as are available from companies such as Chroma) would be optimal.

According to one embodiment of the present invention, the survival replication, differentiation, or death of cells is modulated by electrical activity from Halo. With appropriate light pulses, Halo-expressing cells can be guided down any one of these pathways, depending on the precise pattern of stimulation used to drive activation of Halo. A specific electrical activity pattern results in a specific pattern of downstream signal transduction and in a specific cellular fate response. Therefore, targeting Halo to specific cells, then exposing them to particular light patterns, enables them to be optically driven towards survival, differentiation, replication, or death. This has many potential applications.

For example, in the case where the target cell is a stem cell, particular patterns of activity will drive the replication or differentiation of stem cells (including human embryonic stem cells), or drive the death of the stem cells (in the case where excessive replication is desired to cease). If the target cells are tumor or cancer cells, then targeting Halo to those cells will permit the use of specific and appropriate patterns of light to drive activity, and thus kill the tumor or cancer cells. If the target cells are immune cells, then silencing the cells can prevent the calcium waves that insure cell survival, and reduce the prevalence of autoimmune disease.

Other target cells of this kind may include secretory or organ cells or their precursors, cardiac or other muscle cells, or glial cells in the brain. In each of these cases, it is desirable to control the replication, differentiation, and death of these cells precisely. Halo will be useful for controlling these things in vitro, in vivo in experimental animals, or in vivo in humans (before or after transplantation into the body)—wherever light can be delivered, such as through the skin, via small LEDs, or lasers, or through optical fibers or thin optical endoscopes.

Screening for drugs that modulate ion channel function (e.g., blocking or facilitating ion channel function) can be accomplished using Halo to screen for drugs that modulate ion channel function. One embodiment involves one or more of the following steps:
1) stably express Halo in a cell line;
2) stably express an ion channel of interest ("channel n") in the same cell line;
3) label the cells with a voltage sensitive dye (or other indicator, see below);
4) expose said cells to light, and record the fluorescence of the voltage sensitive dye;
5) expose said cells to a candidate compound that monitors the function of channel n; and
6) expose said cells to light a second time, and record the fluorescence of the voltage sensitive dye.

If the fluorescence is greater during step 6) than step 4), then the candidate drug facilitates channel function. If the fluorescence is smaller during step 6) than step 4), then the candidate drug diminishes channel function. If the fluorescence is equal in steps 4) and 6) (allowing for any bleaching of the dye), then the drug does not affect channel function. In this way, drugs that affect channel function can be detected extremely rapidly.

Steps 1) and 2) of the above process may take several hours or days, but the resulting cell line then suffices for the screening of many (perhaps millions of) drugs, which modulate channel n. Steps 3), 4), 5), and 6) take only a few seconds each; preferably, steps 4), 5), and 6) each take less than 1 second. Steps 4), 5), and 6) take place in a robotic device that moves a 96- or 384-well plate into the focus of an optical beam (see the last section for details on devices). The wells of the plate would all contain the same cell line, in order to facilitate the screening of drugs that affect a particular channel, or each well would contain cells of a different cell line, in order to facilitate the screening of one drug against many different channels ("screening against side effects," see below).

Step 3 can include the use of a voltage-sensitive dye for fast kinetics; however, another dye (e.g., a calcium-sensitive dye in the case that channel n is a calcium channel) could also serve to indicate whether channel function is modulated by the drug. Genetically encoded indicators of voltage or calcium would also be useful for reading out the activity of the cell (e.g., FLASH, GCaMP2, cameleon, etc.). In this case, these indicators would be stably expressed in the cell line as well. Other methods of reading out whether the drug had an effect could also be useful for supplementing this readout (e.g., immunostaining for the phosphorylation of a site that is phosphorylated during or after periods of ion channel activity).

Blindness and other sensory deficits affect millions of people worldwide, severely impacting their quality of life. Halo can be targeted to somatic cells in the human patient to provide a type of sensory prostheses. For example, some forms of blindness destroy photosensor function but leave signal processing in downstream neurons intact. In such diseases, such as macular degeneration or retinitis pigmentosa, targeting Halo to the "off" retinal ganglion cells (e.g., by injecting viruses expressing Halo into the retinal cell layers inside the eye) would enable restoration of visual function. As light increases in the environment, Halo would inhibit the "off" cells, causing increased visual responses in the brain. In such patients treated with Halo targeted to retinal ganglion cells, the retinal ganglion cells would themselves become photosensitive, enabling vision with resolution comparable to the native eye, and not requiring invasive technology beyond that point. Halo is sufficiently sensitive to detect sunlight (power ~1 kW/m^2), with maximal sensitivity in the part of the spectrum that is greatest in sunlight. Expressing Halo in a retinal cell, accompanied with a projection device that would amplify the ambient light, would enable vision inside or in lowlight conditions.

Another implementation of Halo involves situations where the central nervous system neurons in a person are infected with virus expressing Halo (or otherwise come to express Halo). These neurons would then be inhabitable by pulses of yellow light. This gene therapy approach would therefore allow optical inhibition of precise neuronal targets in the brain. If the targeted neurons are epileptic, this would enable silencing of those cells without needing ablative surgery. If the targeted neurons were in the frontal cortex or other parts of the brain, these light-sensitive neurons would permit optical modulation of emotion or cognition. If the targeted neurons were in the spinal cord, neurons that mediate pain stimuli could then be inhibited by light.

In general, such a gene therapy approach opens up a new kind of generalized prosthetic in defined parts of the nervous system. The prosthetic allows light to be converted into neural activity.

In another instance, Halo is targeted to specific and different parts of a cell. For example, targeting Halo to the axon hillock using the AIS (axon initial segment) targeting sequence allows more powerful inhibition. Fusing Halo to a targeting sequence of DNA, so that the resultant protein contains both Halo and the targeting peptide, allows Halo to be sent to the presynaptic terminal, the postsynaptic terminal, the nucleus, or other intracellular compartments. Such targeting sequences include PDZ domains, glutamate and GABA receptor C-terminal sequences, ion channel C-terminal sequences, presynaptic scaffolding targeting sequences, and other targeting sequences. These versions of Halo can then be used to trigger specific intracellular signaling events, including those important for neuroprotection, memory, or other enduring signaling functions.

In a combinatorial fashion, these reagents could complement the other applications of Halo. For example, these reagents could be useful for drug screening (e.g., finding drugs that modulate the function of a channel in a particular subcellular compartment). These reagents could also be useful for prosthetic devices (e.g., driving activity on the dendrites of a neuron, to more closely mimic natural synaptic activity).

Various embodiments, including but not limited to those involving drug screening, employ an optical imaging device containing 1) a light source (LED, lamp, laser) for illuminating the cell expressing Halo and driving a change in cell voltage, 2) a light source for illuminating a dye or indicator, possibly the same light source as used for driving the voltage change, and 3) a switch for alternating between the two light sources or a beamsplitter for simultaneous non-interfering delivery of both kinds of light. The fluorescence of the dye or indicator would be measured by a sensor (CCD camera, PMT, or photodiode). This kind of device can be useful for ion channel drug screening, as described above. The device itself consists of a robotic arm for moving a plate (e.g., a 384-well plate) through the arena where the light sources and sensor are present.

In one embodiment, diagnostic applications, as mentioned herein, use a combined light source imaging device. For example, taking cells from a patient, expressing Halo in them, and then exposing them to light, can be used to reveal patient-specific ion channel syndromes in biopsy samples or in cells of the circulatory system.

For various implementations, an implantable or head-mounted LED, or other small light source can be used. Such a light source can be implanted under the skin, under the skull, deep within the brain, or deep within another organ of interest, in which Halo-expressing cells are also located (either exogenously introduced, or endogenously located and targeted with a virus). This device can be used for stimulating Halo in cells located directly adjacent to the light source. A strip of LEDs, each individually controllable, is useful. For the example of the cortical implant, a 2-dimensional array of LEDs is useful.

For medical applications, various embodiments have LEDs that are remotely powered. A remotely-powered LED can be made, for example, by combining an LED in a closed-loop series circuit with an inductor. This would allow radiofrequency (RF) energy or rapidly changing magnetic fields (e.g., delivered by a transcranial magnetic resonance (TMS) coil) to temporarily power-up the inductor, and thus the connected LED, allowing local delivery of light, even deep in a brain structure. In certain embodiments, such a device is implanted under the skin, under the skull, deep within the brain, or deep within another organ of interest in which Halo-expressing cells are also located (either exogenously introduced, or endogenously located and targeted with a virus). Optionally, another device is used to remotely deliver RF or magnetic energy (e.g., placed nearby or worn on the patient) for activating the implanted device.

*N. pharaonis* halorhodopsin with mammalian-optimized codon usage was synthesized as a DNA sequence according to the sequence listing provided on the following page as Sequence Listing A.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims.

SEQUENCE LISTING A

The *N. pharaonis* halorhodpsin with mammalian-optimized codon usage was synthesized according to the following DNA sequence (876 base pairs).

ATGACTGAGACCCTCCCACCCGTGACTGAAAGCGCCGTCGCTCTGCAAGC

AGAGGTTACCCAGCGGGAGCTGTTCGAGTTCGTCCTCAACGACCCCCTCC

TGGCTTCTAGCCTCTACATCAACATTGCTCTGGCAGGCCTGTCTATACTG

CTGTTCGTCTTCATGACCAGGGGACTCGATGACCCTAGGGCTAAACTGAT

TGCAGTGAGCACAATTCTGGTTCCCGTGGTCTCTATCGCTTCCTACACTG

GGCTGGCATCTGGTCTCACAATCACTGTCCTGGAAATGCCAGCTGGCCAC

TTTGCCGAAGGGAGTTCTGTCATGCTGGGAGGCGAAGAGGTCGATGGGGT

TGTCACAATGTGGGGTCGCTACCTCACCTGGGCTCTCAGTACCCCCATGA

TCCTGCTGGCACTCGGACTCCTGGCCGGAAGTAACGCCACCAAACTCTTC

ACTGCTATTACATTCGATATCGCCATGTGCGTGACCGGGCTCGCAGCTGC

CCTCACCACCAGCAGCCATCTCATGAGATGGTTTTGGTATGCCATCTCTT

GTGCCTGCTTTCTGGTGGTGCTGTATATCCTGCTGGTGGAGTGGGCTCAG

GATGCCAAGGCTGCAGGGACAGCCGACATGTTTAATACACTGAAGCTGCT

CACTGTGGTCATGTGGCTGGGTTACCCTATCGTTTGGGCACTCGCCGTGG

AGGGAATCGCAGTTCTGCCTGTTGGTGTGACAAGCTGGGGCTACTCCTTC

CTGGACATTGTGGCCAAGTATATTTTTGCCTTTCTGCTGCTGAATTATCT

GACTTCCAATGAGTCCGTGGTGTCCGGCTCCATACTGGACGTGCCATCCG

CCAGCGGCACACCTGCCGATGACTGA).

The Halo-GFP fusion protein was generated by PCR amplification of the Halo gene with primers 5'GAATTCGC-CACCATGACTGAGACCCTCCCACCCGTG and 3'GGATCCGTCATCGGCAGGTGTGCCGCTGGC and inserted into the EcoRI and BamHI cites of pEGFP-N3 (Clontech), which has the CMV promoter. The Halo-GFP fusion protein sequence was then PCR amplified with primers 5'CCGGTGCCACCATGACTGAGACCCTCC-CACCCGTG and 3'GAATTCTTACTTGTA-CAGCTCGTCCATCGG and inserted into lentiviral vector FCK(1.3)GW containing the CaMKII promoter via AgeI and EcoRI sites. All constructs were verified by sequencing. The channelrhodopsin construct used in various experiments, FCK-hCmC, contains the human/mammalian codon-optimized gene ChR2 fused to fluorescent protein mCherry, under the CaMKII promoter.

What is claimed is:

1. A method of increasing visual function in a subject suffering from macular degeneration or retinitis pigmentosa, the method comprising:
   expressing a light-driven chloride ion pump from *Natronobacterium pharaonis* (NpHR) in retinal layers of the eye of a subject; and
   exposing the subject to yellow light to activate the expressed NpHR ion pump,
   wherein the activation of the NpHR ion pump in response to yellow light inhibits depolarization of the retinal ganglion cells, thereby increasing visual responses in the brain of the subject.

2. The method of claim 1, wherein the NpHR is encoded by a nucleotide sequence that is operably linked to a neuron specific promoter.

3. The method of claim 1, wherein the method further comprises amplifying the light with a projection device.

4. The method of claim 1, wherein the light has an intensity of about 10 mW/mm$^2$.

5. The method of claim 1, wherein the light has an intensity of about 1 kW/m$^2$.

6. A method of inducing hyperpolarizing of a retinal ganglion cell, the method comprising:
   expressing a light-driven chloride ion pump from *Natronobacterium pharaonis* (NpHR); and
   exposing the retinal ganglion cell to yellow light to activate the expressed NpHR ion pump, thereby decreasing the probability of depolarization events occurring in the retinal ganglion cell.

7. The method of claim 6, wherein the retinal ganglion cell is in vitro.

8. The method of claim 6, wherein the retinal ganglion cell is in vivo.

9. The method of claim 6, wherein the NpHR ion pump is encoded by a mammalian codon-optimized nucleotide sequence.

10. The method of claim 6, wherein the NpHR ion pump is encoded by a nucleotide sequence that is operably linked to a CaMKII promoter.

11. The method of claim 6, wherein the light has a wavelength of around 560 nm.

12. The method of claim 6, wherein the light is provided by an implantable light source.

13. The method of claim 6, wherein the light is provided by a light-emitting diode (LED).

* * * * *

SEQUENCE LISTING

<160> NUMBER OF SEQ ID NOS: 5

<210> SEQ ID NO 1
<211> LENGTH: 876
<212> TYPE: DNA

<213> ORGANISM: Artificial Sequence
<220> FEATURE:
<223> OTHER INFORMATION: mammalian codon-optimized sequence from Natronobacterium pharaonis

<400> SEQUENCE: 1

```
atgactgaga ccctcccacc cgtgactgaa agcgccgtcg ctctgcaagc agaggttacc      60
cagcgggagc tgttcgagtt cgtcctcaac gacccctcc tggcttctag cctctacatc     120
aacattgctc tggcaggcct gtctatactg ctgttcgtct tcatgaccag ggactcgat     180
gaccctaggg ctaaactgat tgcagtgagc acaattctgg ttcccgtggt ctctatcgct     240
tcctacactg ggctggcatc tggtctcaca atcagtgtcc tggaaatgcc agctggccac     300
tttgccgaag ggagttctgt catgctggga ggcgaagagg tcgatggggt tgtcacaatg     360
tggggtcgct acctcacctg ggctctcagt accccccatga tcctgctggc actcggactc     420
ctggccggaa gtaacgccac caaactcttc actgctatta cattcgatat cgccatgtgc     480
gtgaccgggc tcgcagctgc cctcaccacc agcagccatc tgatgagatg gttttggtat     540
gccatctctt gtgcctgctt tctggtggtg ctgtatatcc tgctggtgga gtgggctcag     600
gatgccaagg ctgcagggac agccgacatg tttaatacac tgaagctgct cactgtggtg     660
atgtggctgg gttaccctat cgtttgggca ctcggcgtgg agggaatcgc agttctgcct     720
gttggtgtga caagctgggg ctactccttc ctggacattg tggccaagta tattttgcc     780
tttctgctgc tgaattatct gacttccaat gagtccgtgg tgtccggctc catactggac     840
gtgccatccg ccagcggcac acctgccgat gactga                              876
```

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2

```
gaattcgcca ccatgactga gaccctccca cccgtg                               36
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3

```
ggatccgtca tcggcaggtg tgccgctggc                                      30
```

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4

```
ccggtgccac catgactgag accctcccac ccgtg                                35
```

<210> SEQ ID NO 5
<211> LENGTH: 30
<212> TYPE: DNA
<213> ORGANISM: Artificial Sequence
<220> FEATURE:

```
<223> OTHER INFORMATION: primer

<400> SEQUENCE: 5
gaattcttac ttgtacagct cgtccatcgg                                            30
```